US005722412A

United States Patent [19]
Pflugrath et al.

[11] Patent Number: 5,722,412
[45] Date of Patent: Mar. 3, 1998

[54] HAND HELD ULTRASONIC DIAGNOSTIC INSTRUMENT

[75] Inventors: Lauren S. Pflugrath, Seattle; Jacques Souquet, Issaquah, both of Wash.

[73] Assignee: Advanced Technology Laboratories, Inc., Bothell, Wash.

[21] Appl. No.: 672,782

[22] Filed: Jun. 28, 1996

[51] Int. Cl.$^6$ .................................................. A61B 8/00
[52] U.S. Cl. ................................................ 128/662.03
[58] Field of Search .................. 128/660.07, 660.08, 128/660.01, 661.1, 660.09, 662.03, 660.04, 660.05, 661.08, 661.09

[56] References Cited

U.S. PATENT DOCUMENTS 5,295,485  3/1994  Shinomura et al. ............. 128/660.07
5,590,658  1/1997  Chiang et al. ................... 128/661.01

OTHER PUBLICATIONS

Minivisor Service Manual from Organon Teknika (Sep. 1979).

Ultra PCI System Specifications from Advanced Medical Products of Columbia, South Carolina (date unknown).

*Primary Examiner*—George Manuel
*Attorney, Agent, or Firm*—W. Brinton Yorks, Jr.

[57] ABSTRACT

A hand held ultrasonic instrument is provided in a portable unit which performs both B mode and Doppler imaging. In a preferred embodiment an array transducer, digital beamformer, digital filter, and image processor are packaged in one or more enclosures weighing ten pounds (4.5 kilograms) or less.

24 Claims, 19 Drawing Sheets

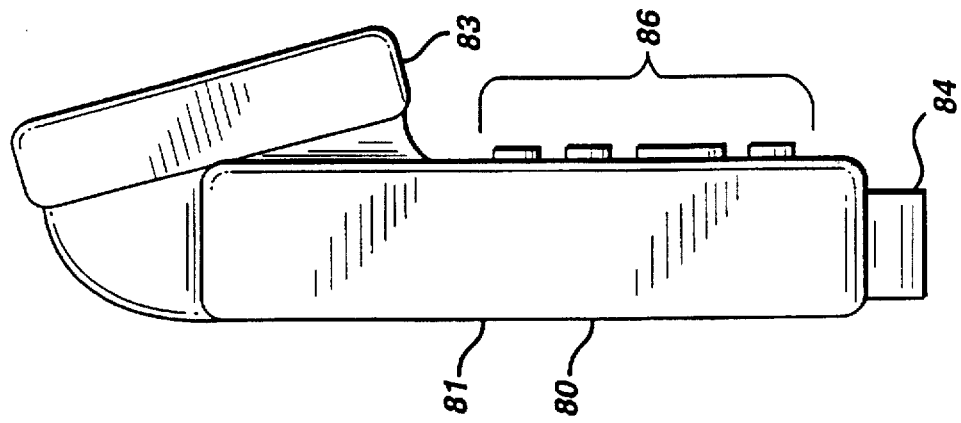
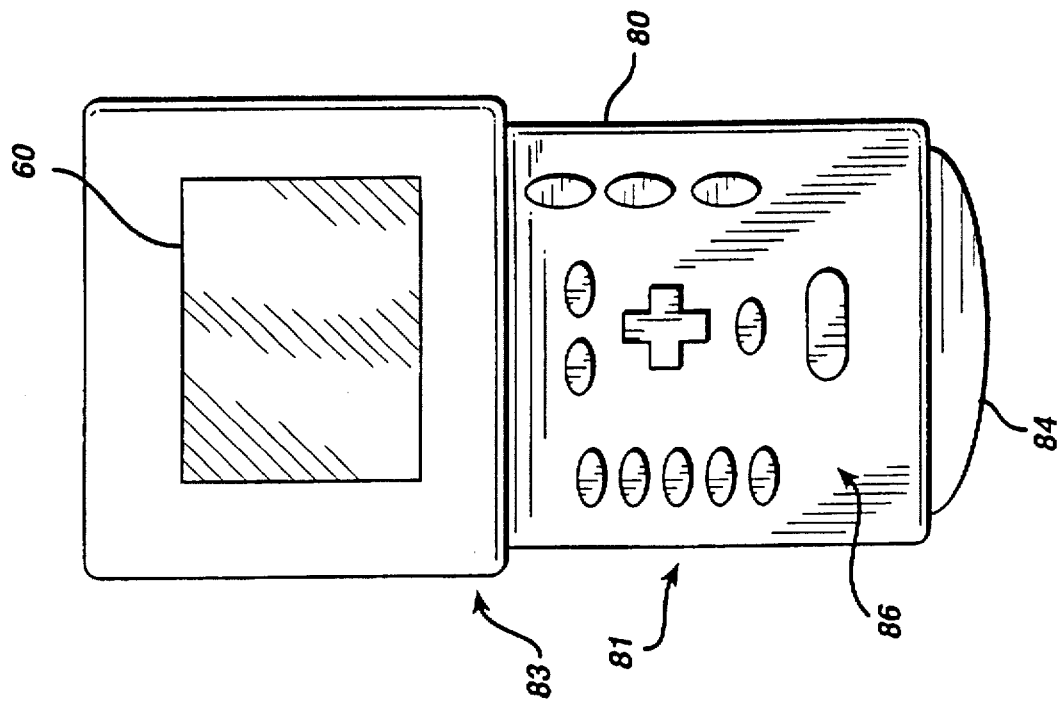

FIG.22

| SWITCH FUNCTION | | DESCRIPTION | NUMBER OF CONTACTS |
|---|---|---|---|
| POWER OFF/ON | ⊂⊃ | SLIDE SWITCH | 1 |
| ACTIVE SCAN/FREEZE | ◯ | PUSH AND HOLD FOR ACTIVE SCAN | 1 |
| CPA | ◯ | ENABLES AND DISABLES COLOR POWER ANGIO CPA | 1 |
| DOPPLER/CPA FILTER | ◯ | HIGH/MEDIUM/LOW BUTTON CYCLES THROUGH 3 SELECTIONS | 1 |
| 3D IMAGING MODE | ◯ | ENABLES 3D CAPTURE WHEN ENGAGED BEFORE THE ACTIVE SCAN BUTTON IS PUSHED | 1 |
| PRINT | ◯ | SENDS SERIAL SIGNAL TO PRINTER | 1 |
| CURSOR POSITION | ✛ | X/Y POSITION OF CURSOR | 4 |
| ENTER | ◯ | ENTERS SELECTION | 1 |
| MENU | ◯ | TOGGLES MENU FUNCTIONS OFF AND ON, USES CURSOR AND ENTER. FUNCTIONS: APPLICATION SELECTION USED TO ENTER ALPHA NUMERIC DATA, PATIENT ID, PATIENT NAME, CINE 2D AND 3D REVIEW | 1 |
| MEASURE | ◯ | ENABLES MEASUREMENTS, USES CURSOR AND ENTER | 1 |
| FOCUS | ◯ | ENABLES FOCUS MODE, CURSOR UP DOWN POSITIONS FOCUS, CURSOR LEFT RIGHT SELECTS NUMBER OF ZONES | 1 |
| IMAGE | ◯◯ | ALLOWS THE USER TO SELECT THROUGH SEVERAL GRAY SCALE CURVES, SPATIAL AND TEMPORAL FILTERS WITH IN A PREDETERMINED SET OF SETUPS FOR A SELECTED APPLICATION | 2 |
| DEPTH | ◯◯ | UP/DOWN, 5 DEPTH SELECTIONS | 2 |
| TGC GAIN | ◯◯ | UP/DOWN | 2 |
| BRIGHTNESS | ◯◯ | LCD DISPLAY CONTROL UP/DOWN | 2 |
| CONTRAST | ◯◯ | LCD DISPLAY CONTROL UP/DOWN | 2 |

HAND HELD ULTRASONIC DIAGNOSTIC INSTRUMENT

This invention relates to medical ultrasonic diagnostic systems and, in particular, to a fully integrated hand held ultrasonic diagnostic instrument.

As is well known, modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., assignee of the present invention, were smaller, desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

However, with the ever increasing density of digital electronics, it is now possible to foresee a time when ultrasound systems will be able to be miniaturized to a size even smaller than their much earlier ancestors. The physician is accustomed to working with a hand held ultrasonic scanhead which is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

In accordance with the principles of the present invention, a diagnostic ultrasound instrument is provided which exhibits many of the features of a premium ultrasound system in a hand held unit. The instrument can be produced as a single unit or, in a preferred embodiment, the instrument is a two-part unit, one including a transducer, beamformer, and image processor and the other including a display and power source for both units. In such a configuration the transducer/processor unit can be manipulated with one hand while a cable between the two units enables the video to be shown on the display unit while the latter unit is held or positioned for optimal viewing of the ultrasound image. The cable also provides energy for the transducer/processor unit from the display unit.

In a preferred embodiment the ultrasound system, from the transducer through to a video output, is fabricated on four types of application specific integrated circuits (ASICs): a transmit/receive ASIC which is connected to the elements of an array transducer, a front end ASIC which performs and controls transmit and receive beamforming, a digital signal processing ASIC which provides processing of the ultrasound signals such as filtering, and a back end ASIC which receives processed ultrasound signals and produces ultrasound image data. The image can be displayed on either a standard monitor or on a liquid crystal display (LCD). Comprised as it is of ASICs, the electronics of the unit can be fabricated on a single printed circuit board, eliminating the problems conventionally posed by connectors and cables. This sophisticated ultrasound instrument can be manufactured as a hand held unit weighing less than five pounds.

In the drawings:

FIGS. 2a and 2b are front and side views of a hand-held ultrasound system of the present invention which is packaged as a single unit;

FIG. 22 is a chart of the user controls of the ultrasound system of FIG. 1.

Figure 1:
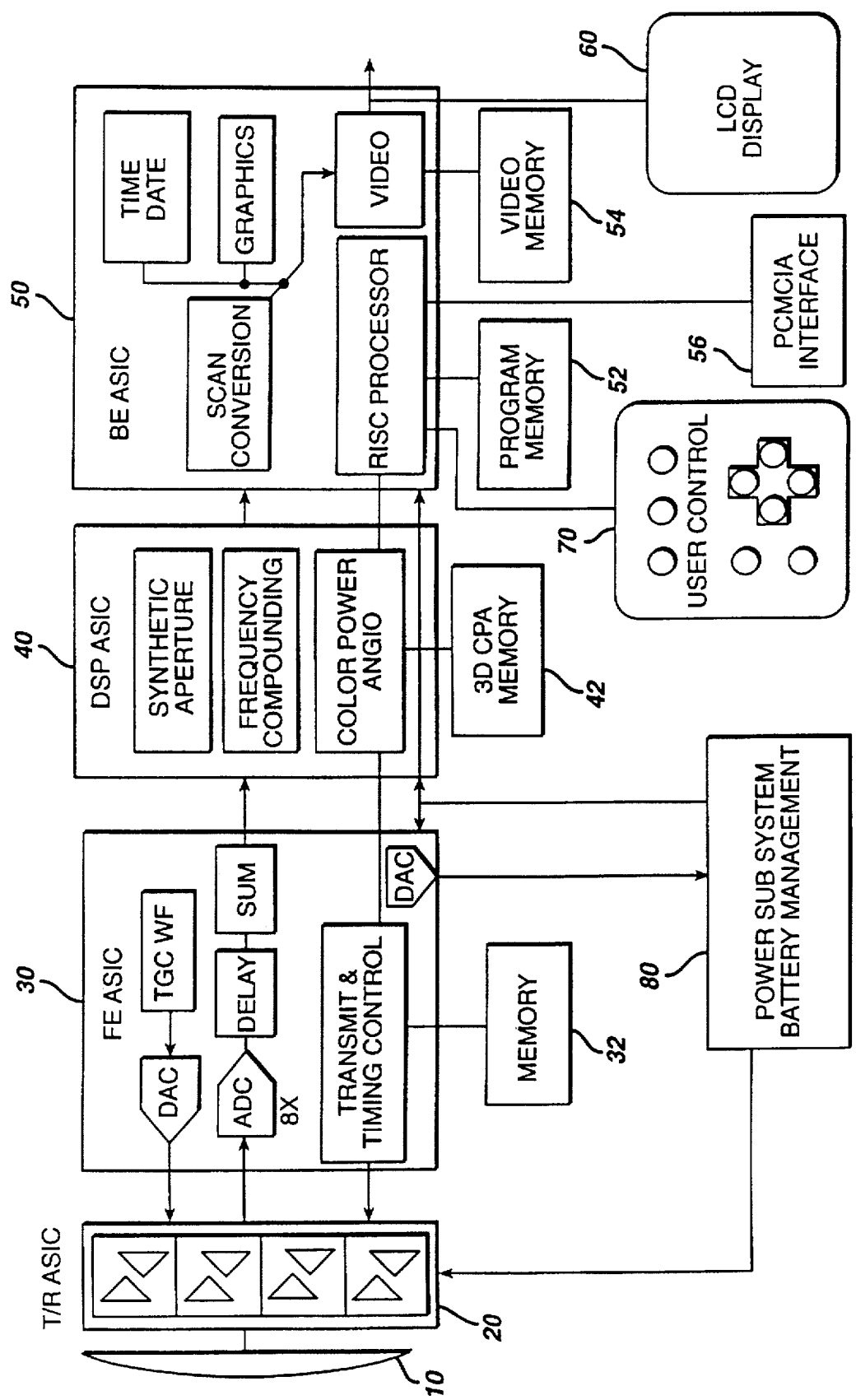
FIG. 1 illustrates in block diagram form the architecture of a hand-held ultrasound system of the present invention.

Referring first to FIG. 1, the architecture of a hand-held ultrasound system of the present invention is shown. It is possible to package an entire ultrasound system in a single hand-held unit only through judicious selection of functions and features and efficient use of integrated circuit and ultrasound technology. A transducer array 10 is used for its solid state, electronic control capabilities, variable aperture, image performance and reliability. Either a flat or curved linear array can be used. In a preferred embodiment the array is a curved array, which affords a broad sector scanning field. While the preferred embodiment provides sufficient delay capability to both steer and focus a flat array such as a phased array, the geometric curvature of the curved array reduces the delay requirements on the beamformer. The elements of the array are connected to a transmit/receive ASIC 20 which drives the transducer elements and receives echoes received by the elements. The transmit/receive ASIC 30 also controls the transmit and receive apertures of the array 10 and the gain of the received echo signals. The transmit/receive ASIC is preferably located within inches of the transducer elements, preferably in the same enclosure, and just behind the transducer.

Echoes received by the transmit/receive ASIC 20 are provided to the adjacent front end ASIC 30, which beamforms the echoes from the individual transducer elements into scanline signals. The front end ASIC 30 also controls the transmit waveform, timing, aperture and focusing. In the illustrated embodiment the front end ASIC 30 provides timing signals for the other ASICs, time gain control, and monitors and controls the power applied to the transducer array, thereby controlling the acoustic energy which is applied to the patient and minimizing power consumption of the unit. A memory device 32 is connected to the front end ASIC 30, which stores data used by the beamformer.

Beamformed scanline signals are coupled from the front end ASIC 30 to the adjacent digital signal processing ASIC 40. The digital signal processing ASIC 40 filters the scanline signals and in the preferred embodiment also provides several advanced features including synthetic aperture formation, frequency compounding, Doppler processing such as power Doppler (color power angio) processing, and speckle reduction.

The ultrasound B mode and Doppler information is then coupled to the adjacent back end ASIC 50 for scan conversion and the production of video output signals. A memory device 42 is coupled to the back end ASIC 50 to provide storage used in three dimensional power Doppler (3D CPA) imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in a live Cineloop® realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set controller) processor. The RISC processor is coupled to the front end and digital signal processing ASICs to control and synchronize the processing and control functions throughout the hand-held unit. A program memory 52 is coupled to the back end ASIC 50 to store program data which is used by the RISC processor to operate and control the unit. The back end ASIC 50 is also coupled to a data port configured as a PCMCIA interface 56. This interface allows other modules and functions to be attached to the hand-held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand-held ultrasound system.

Power for the hand-held ultrasound system in a preferred embodiment is provided by a rechargeable battery. Battery power is conserved and applied to the components of the unit from a power subsystem 80. The power subsystem 80 includes a DC converter to convert the low battery voltage to a higher voltage which is applied to the transmit/receive ASIC 20 to drive the elements of the transducer array 10.

FIGS. 2a and 2b illustrate a one piece unit 80 for housing the ultrasound system of FIG. 1. The front of the unit is shown in FIG. 2a, including an upper section 83 which includes the LCD display 60. The lower section 81 includes the user controls as indicated at 86. The user controls enable the user to turn the unit on and off, select operating characteristics such as the mode (B mode or Doppler), color Doppler sector or frame rate, and special functions such as three dimensional display. The user controls also enable entry of time, date, and patient data. A four way control, shown as a cross, operates as a joystick to maneuver cursors on the screen or select functions from a user menu. Alternatively a mouse ball or track pad can be used to provide cursor and other controls in multiple directions. Several buttons and switches of the controls are dedicated for specific functions such as freezing an image and storing and replaying an image sequence from the Cineloop memory.

At the bottom of the unit 80 is the aperture 84 of the curved transducer array 10. In use, the transducer aperture is held against the patient to scan the patient and the ultrasound image is displayed on the LCD display 60.

FIG. 2b is a side view of the unit 80, showing the depth of the unit. The unit is approximately 20.3 cm high, 11.4 cm wide, and 4.5 cm deep. This unit contains all of the elements of a fully operational ultrasound system with a curved array transducer probe, in a single package weighing less than five pounds. A major portion of this weight is attributable to the battery housed inside the unit.

Figure 4:
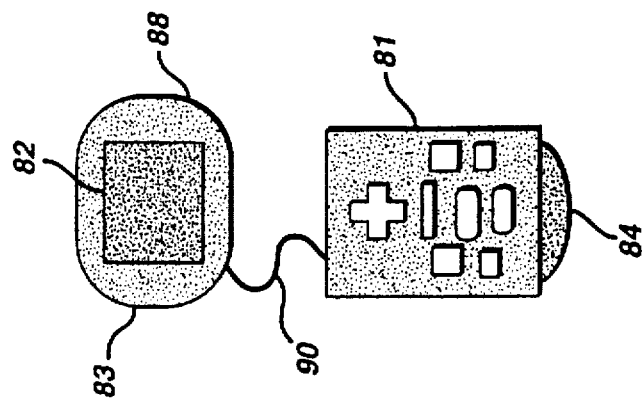
FIG. 4 illustrates the two units of a hand-held ultrasound system of the present invention in a two-unit package.
Figure 3B:
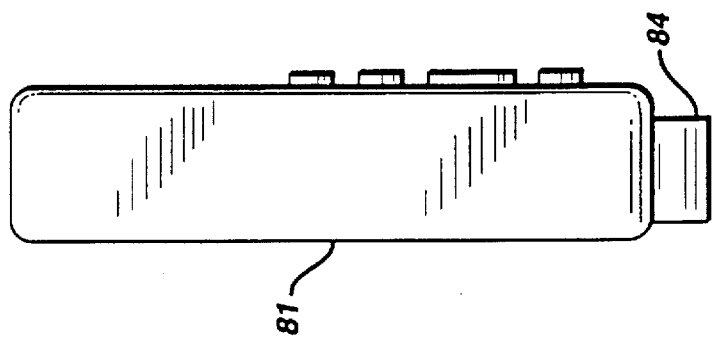
FIGS. 3a and 3b are front and side views of the transducer unit of a two-unit hand-held ultrasound system of the present invention.
Figure 3A:
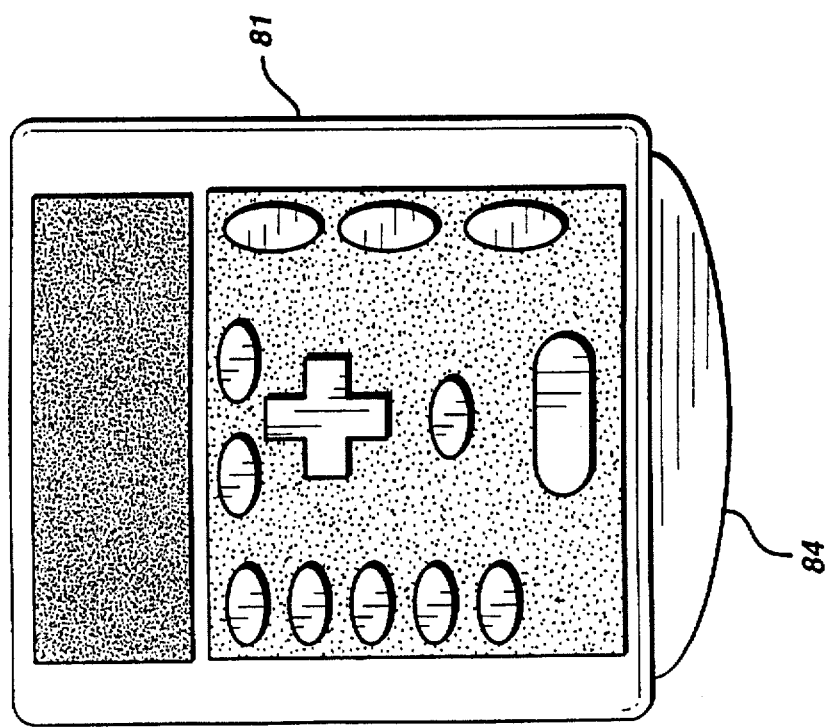

FIGS. 3 and 4 illustrate a second packaging configuration in which the ultrasound system is housed in two separate sections. A lower section 81 includes the transducer array, the electronics through to a video signal output, and the user controls. This lower section is shown in FIG. 3a, with the curved transducer array aperture visible at the bottom. The lower section is shown in the side view of FIG. 3b. This lower section measures about 11.4 cm high by 9.8 cm wide by 2.5 cm deep. This unit has approximately the same weight as a conventional ultrasound scanhead. This lower section is connected to an upper section 83 as shown in FIG. 4 by a cable 90. The upper section 83 includes an LCD display 82 and a battery pack 88. The cable 90 couples video signals from the lower unit 81 to the upper unit for display, and provides power for the lower unit from the battery pack 88. This two part unit is advantageous because the user can maneuver the lower unit and the transducer 84 over the patient in the manner of a conventional scanhead, while holding the upper unit in a convenient stationary position for viewing. By locating the battery pack in the upper unit, the lower unit is lightened and easily maneuverable over the body of the patient.

Other system packaging configurations will be readily apparent. For instance, the front end ASIC 30, the digital signal processing ASIC 40, and the back end ASIC 50 could be located in a common enclosure, with the beamformer of the front end ASIC connectable to different array transducers. This would enable different transducers to be used with the digital beamformer, digital filter, and image processor for different diagnostic imaging procedures. A display could be located in the same enclosure as the three ASICS, or the output of the back end ASIC could be connected to a separate display device.

Figure 5:
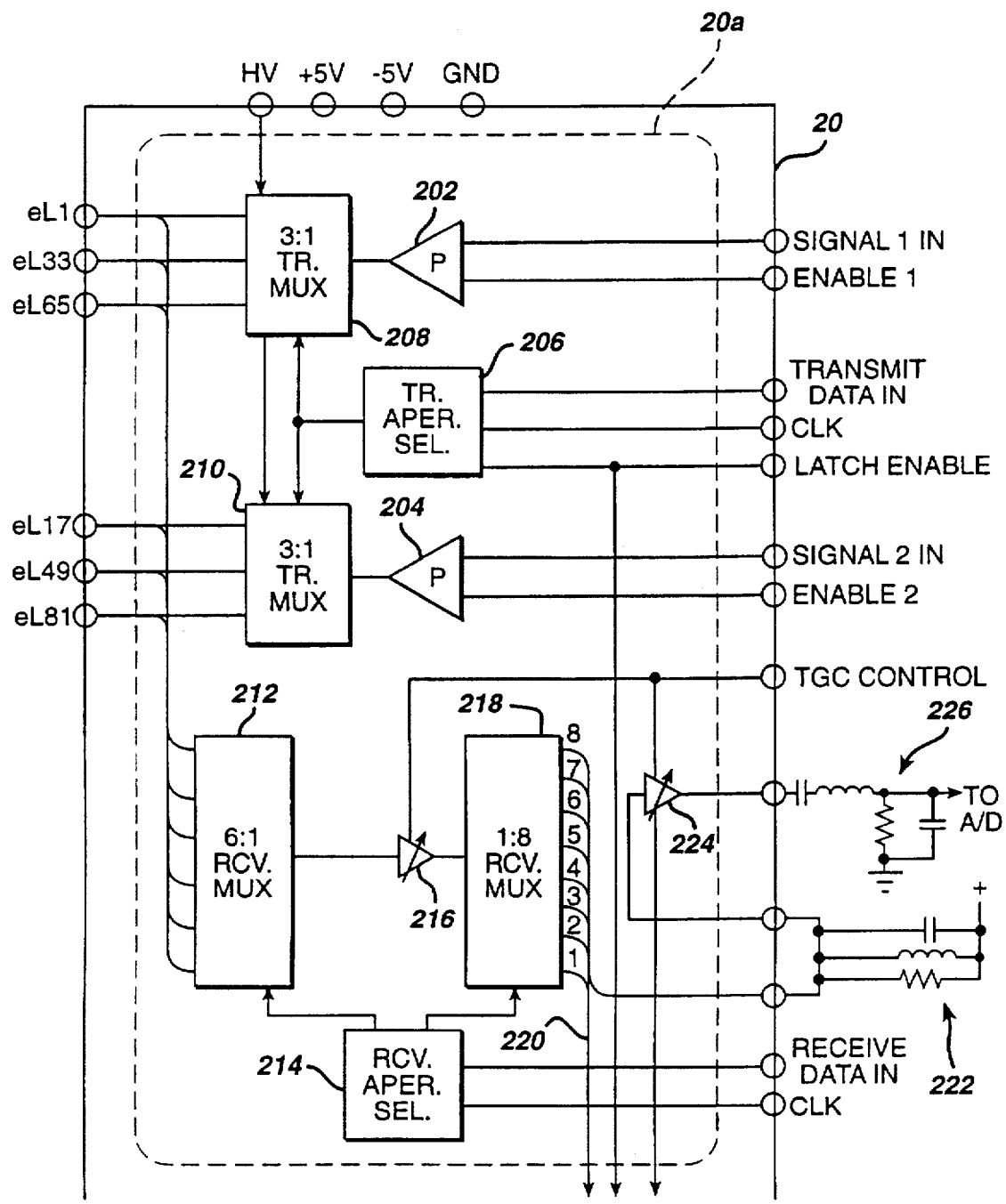
FIG. 5 is a schematic diagram of the transmit/receive ASIC of the ultrasound system of FIG. 1.

Referring now to FIG. 5, the transmit/receive ASIC 20 is shown in greater detail. This ASIC is comprised of sixteen sections, each of which is coupled to six transducer elements of the array 10. The illustrated section 20a is coupled to elements 1, 17, 33, 49, 65 and 81 at the terminals on the left side of the drawing. With six elements per section, the entire ASIC can operate with a 96 element transducer. Each section could be configured to operate with eight elements, in which case the ASIC could control a 128 element transducer, for instance. Prior to the transmission of an ultrasonic pulse for a scanline, a serial stream of data from the front end ASIC 30 is clocked into transmit aperture select logic 206 at the Transmit Data In and Clk terminals at the right side of the drawing. The transmit aperture select logic 206 uses this data to set multiplexer switches in 3:1 transmit muxes 208 and 210 for the transducer elements that will be active for the particular scanline. For instance, the next scanline to be transmitted may have a transmit aperture comprising elements 1–32. This requires that transmit mux 208 closes a switch to connect pulser 202 to the element 1 terminal, and the transmit mux 210 closes a switch to connect pulser 204 to the element 17 terminal. In a similar manner the transmit muxes in the other fifteen sections of the ASIC will connect pulsers to element terminals 2–16 and 18–32.

At the times when the connected elements 1 and 17 are to be activated, drive signals for the pulsers 202 and 204 are applied to the Signal 1 In and Signal 2 In terminals by the front end ASIC. For unipolar pulsers the drive signals may be applied to these terminals, then the pulsers are enabled at the appropriate times by signals applied to the enable 1 and enable 2 terminals. Alternatively, complementary waveforms are applied at the appropriate times to the paired terminals. These drive signals are applied as logic level signals to the pulser inputs, then converted to high voltage driving waveforms by the application of high voltage HV applied to the muxes 208 and 210. It is also possible to fabricate the pulser and mux functions as a single unit, whereby each switch of the muxes is effectively a high voltage pulser. Stated another way, this means that each mux would comprise three separately controlled pulsers. Alternatively, the two pulsers at the inputs of the transmit muxes could be deleted and replaced by six pulsers at the outputs of the transmit muxes, however, the illustrated embodiment advantageously requires only two, low voltage pulsers. Continuing with the example of the aperture of elements 1–32, if element 1 is at the periphery of the aperture and element 17 is more central to the aperture, element 1 would be pulsed earlier in time than element 17 to produce a focused transmitted ultrasonic waveform.

Prior to transmission of the scanline a stream of digital data from the front end ASIC is clocked into receive aperture select logic 214 from the Receive Data In and Clk terminals connected to logic 214. The receive aperture select logic closes switches in a 6:1 receive mux 212 and a 1:8 receive mux 218 for the proper receive aperture. Like the transmit aperture select logic, the receive aperture select logic includes buffer storage so that data for the next scanline can be received while the ASIC is receiving echoes from the current scanline. The illustrated embodiment is designed for a sixteen element folded receive aperture as shown by the eight data bus lines at the output of the 1:8 receive mux 218. The inputs to the 6:1 receive mux 212 are connected to the six element terminals for section 201 and are protected from the high drive voltages by the integration of transmit/receive networks at the mux inputs. The receive aperture select logic 214 connects one of the inputs of the mux 212 to the mux output, and the received signal from the selected element is applied to a first time gain control (TGC) amplifier 216. The gain of this TGC amplifier is controlled by a control signal applied to a TGC Control terminal of the ASIC. The amplification provided by amplifier 216 increases as ultrasonic echoes are received from increasing depths, in the conventional manner. The amplified echo signals are then coupled by the switching of the 1:8 receive mux 218 to one of the data bus lines 220.

Each of the data bus lines 220 is coupled to the same corresponding output of every 1:8 receive mux on the ASIC. The outputs of the mux 218 are numbered from 1–8. Output 1 of each 1:8 receive mux is coupled to the same one of the data lines; output 2 of each 1:8 receive mux is coupled to another one of the data lines; and so forth. The preferred embodiment system uses a sixteen element folded aperture of scanlines transmitted orthogonal to the transducer. This means that two elements of the aperture will have the same receive phases of operation; the sixteen elements of the receive aperture will be paired to have eight receive phases. For instance, if the received scanline is located at the center of an aperture of elements 1–16, elements 1 and 16 will have the same receive timing. Echoes received by element 1 will be connected through mux 212, amplified by TGC amplifier 216, connected through mux 218 and produced as a current output at output 8 of the mux 218. At the same time, an echo received by element 16 will be connected through the muxes of another section of the ASIC, identically amplified by another TGC amplifier, and produced as a current output at output 8 of another 1:8 receive mux. These two currents are identically phased by virtue of the folded aperture, and combine on the data line which is coupled to output 8 of the receive muxes.

The currents on each data line are filtered and converted to voltages by a filter network such as that shown at 222. In the preferred embodiment filter network 222 is external to and coupled to a terminal of the ASIC so that its components and hence its filter characteristic can be easily selected and changed. The filter characteristic is a bandpass chosen to match the passband of the transducer. For a 3.5 MHz transducer the passband could extend from 1.5 to 5.5 MHz, for example. The filter is connected to a current source through the filter impedance to convert the current signals to a single voltage. This voltage reenters the ASIC through another (or the same) ASIC terminal and is applied to the input of a second TGC amplifier 224. The use of two TGC amplifiers enables operation over the wide dynamic range of the two cascaded amplifiers. In the illustrated embodiment a single TGC Control applies the same control characteristic to both TGC amplifiers 216 and 224, but it is also possible to apply separate and different TGC characteristics to the two amplifiers. The amplified echo signals are brought to a final output terminal of the ASIC where they are filtered by a bandpass filter 226 and coupled to an analog to digital (A/D) converter at the input of the beamformer on the front end ASIC.

The separate sections of the transmit/receive ASIC 20 may be contained in separate ASICs or combined so that several sections are integrated on the same ASIC. Preferably all sixteen sections are integrated onto a single ASIC chip.

Thus it is seen that, in the preferred embodiment, the transmit/receive ASIC 20 operates with a 96 element transducer array, and uses a 32 element transmit aperture and a 16 element folded receive aperture. With the use of a synthetic aperture as discussed below, the system exhibits a 32 element aperture on both transmit and receive.

Figure 6:
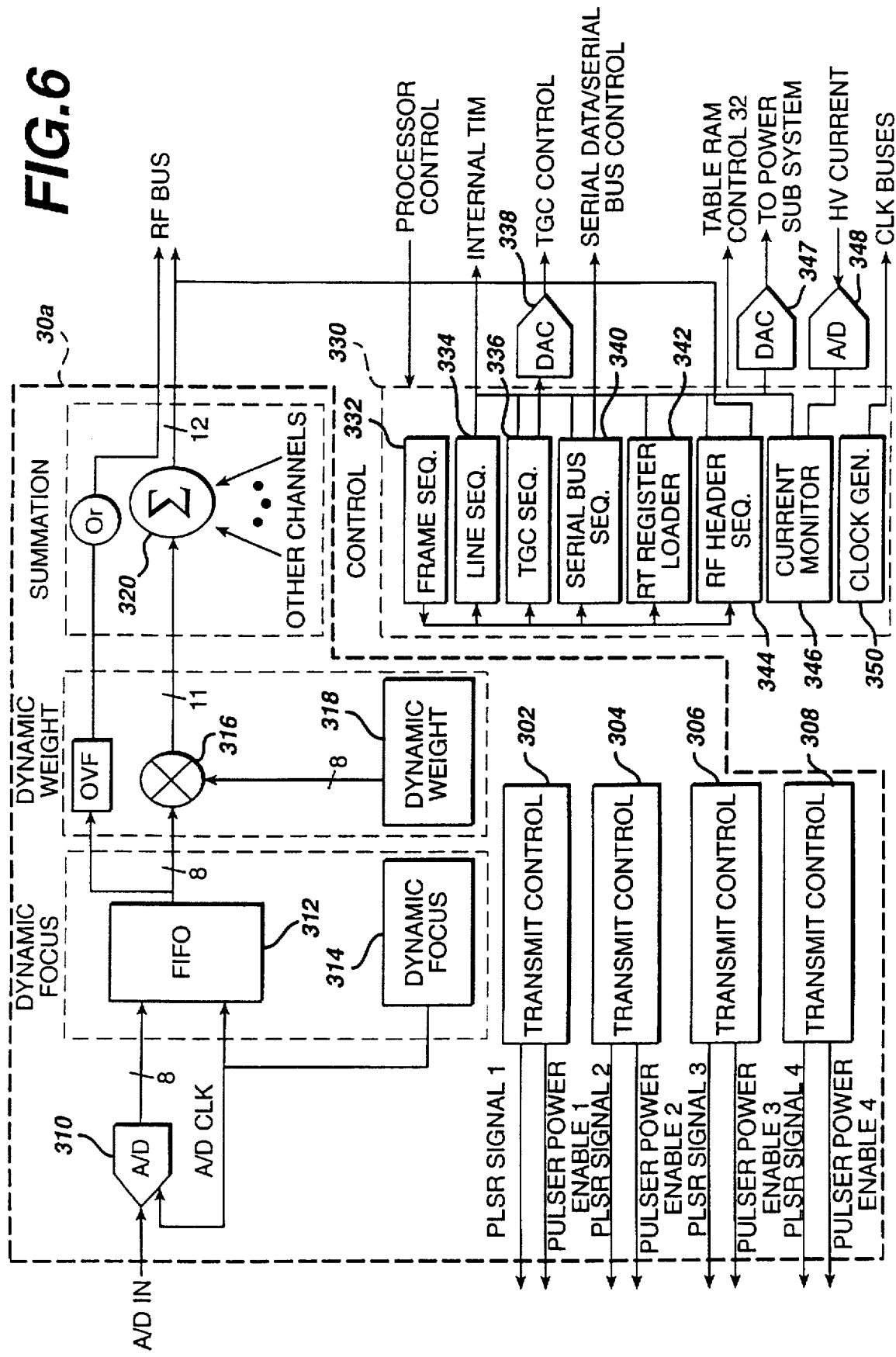
FIG. 6 is a block diagram of the front end ASIC of the ultrasound system of FIG. 1.

Details of the front end ASIC 30 are shown in FIG. 6. This drawing shows one section 30a of the front end ASIC 30. There are eight such sections on the front end ASIC to provide beamforming of the eight outputs from the transmit/receive ASIC 20. Each echo signal output is coupled to the input of an A/D converter 310, where the echo signals are converted to digital data. The digital data from each element (or each pair of elements in a folded aperture) is shifted into a first in, first out (FIFO) register 312 by a clock signal A/D CLK. The A/D CLK signal is provided by a dynamic focus timing circuit 314 which defers the start of the clock signal to provide an initial delay, then controls the signal sampling times to provide dynamic focusing of the received echo signals. The length of the FIFO register 312 is determined by the initial delay, the transducer center frequency, the aperture size, the curvature of the array, and the beam steering requirement. A higher center frequency and a curved array will reduce the delay requirement and hence the length of the FIFO register, for instance. The delayed echo signals from the FIFO register 312 are coupled to a multiplier 316 where the echo signals are weighted by dynamic weight values stored in a dynamic weight register 318. The dynamic weight values weight the echo signals to normalize the echo information in consideration of the effects of a dynamic receive aperture, which expands by the inclusion of additional outer elements as echoes are received from increasing depths along the scanline. The delayed and weighted echo signals are then summed with appropriately delayed and weighted echo signals from other elements and echo signals from any other delay stages which are coupled in cascade by a summing circuit 320. The beamformed echo signals, together with synchronous overflow bits, are produced as output scanline data on an RF data bus. Accompanying each output sequence of scanline echo signals is identifying information provided by an RF header sequencer on the ASIC, which identifies the type of scanline data being produced. The RF header can identify the scanline as B mode echo data or Doppler data, for instance.

Other digital storage devices can be used to provide the beamformer delays, if desired. A dual ported random access memory can be used to store the received digital echo samples, which are then read out from the memory at times or sequences which provide the desired delay for the signals from the transducer elements.

Each section 30a of the front end ASIC includes transmit control circuits 302–308 for four transducer elements of the array. The eight sections thus provide transmit control for 32 elements of the array at the same time, thereby determining the maximum transmit aperture. The transmit control circuits produce waveforms at the desired transmission frequency, and enable signals which activate the pulsers at the appropriate times to produce a transmitted acoustic signal which is focused at the desired depth of focus.

The front end ASIC includes a common control section 330 which provides overall control for the transmission and receive functions. The control section 330 is controlled by and receives data under control of the RISC processor located on the back end ASIC. The data tables for a particular image frame are stored in random access memory (RAM) 32 and are loaded into the control section 330 under command of the RISC processor. The control section 330 includes a number of sequencers for the sequence of transmit and receive functions. The frame sequencer 332 produces information used by other sequencers which identifies the type of image frame which is to be produced. The frame sequencer may, for example, be loaded with data that defines the next frame as B mode scanlines interspersed between groups of four Doppler scanlines, and that the sequence of scanlines will be all odd numbered scanlines followed by all even numbered scanlines. This information is supplied to the line sequencer 334, which controls the scanlines which are transmitted and received in the proper sequence. In preparation for a new scanline the line sequencer controls the TGC sequencer 336 so that it will produce the desired sequence of TGC control data. The TGC control data from the TGC sequencer is converted to a voltage signal by a digital to analog converter (DAC) 338 and applied to the TGC Control input terminal(s) of the transmit/receive ASIC 20. The line sequencer 334 also controls the serial bus sequencer 340, which produces serial data on a serial bus for the transmit and receive aperture select logic circuits 206 and 214 on the transmit/receive ASIC. The receive/transmit (RT) register loader 342 controls the loading of data for a new scanline into various registers on both ASICs, including the aperture select logic circuits 206 and 214, the transmit control circuits 302–308, the dynamic focus timing circuit 314 and the dynamic weight register 318. All registers which perform real time functions are double buffered. As discussed above, the various registers are buffered so that the control data can be put on the serial bus and loaded into the various registers during the line preceding the scanline for which the control data is used.

The front end ASIC 30 includes a current monitor circuit 346, which samples the current on the HV bus by way of an A/D converter 348. The current monitor assures patient safety by reducing or completely shutting down the high voltage supply if excessive current levels are detected, thereby protecting the patient from an overheated transducer or unacceptably high acoustic output levels.

The front end ASIC includes in its control section a clock generator 350 which produces a plurality of synchronous clock signals from which all operations of the system are synchronized. To prevent interference and crosstalk among the closely spaced devices of the system, the scanline transmission frequency is synchronized to the video output signal frequency, so harmonics of one frequency will not produce interfering components in the other. A crystal oscillator (not shown) is coupled to the front end ASIC 30 to provide a basic high frequency such as 60 MHz from which all of the clock signals of the system may be derived.

Figure 7:
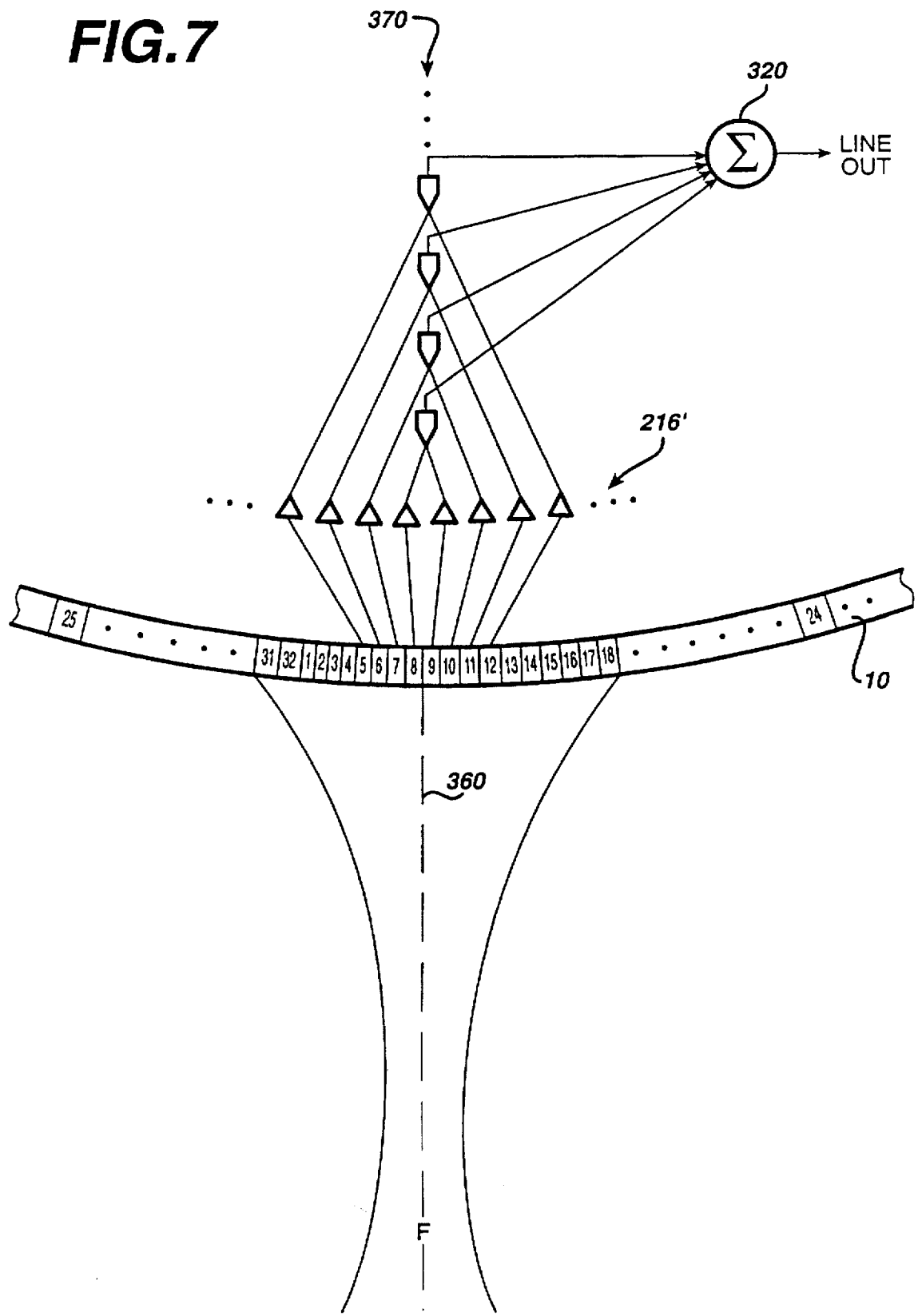
FIG. 7 illustrates the aperture control afforded by the transmit/receive and front end ASICs.

The operation of the transmit/receive and front end ASICs 20 and 30 to produce a synthetic folded aperture scanline from 32 elements of a curved array is illustrated with reference to FIG. 7. In this drawing the ASICs are controlling an aperture of the transducer comprising 32 elements numbered from 25 through 32, then 1 through 24 of the curved array 10. Gathering the full aperture of scanline information requires two transmit sequences of all 32 elements. To transmit, the line sequencer 334, the serial bus sequencer 340, and the RT register loader 342 load the proper transmit mux data into the sixteen transmit aperture select logic circuits 206 and the 32 transmit controllers on the front end ASIC. The aperture select logic then control the 32 transmit muxes to connect pulsers to elements numbered 25–32 and 1–24, the desired transmit aperture. The pulsers are pulsed by the transmit control circuits so as to produce an acoustic wave which is focused at point F in FIG. 7.

Following the first pulse transmission, echoes are received by the center group of elements numbered 1–16, which at that time are connected by the sixteen 6:1 receive muxes and 1:8 receive muxes to eight output data lines. The sixteen receive signals are shown as separate when they pass through the initial TGC amplifiers, eight of which are shown in a row as indicated at 216' in FIG. 7. The like phased signals are then seen to combine in pairs by virtue of the folded aperture where pairs of lines come together at the input of the beamformer delay lines, four of which are shown as indicated at 370. In the illustrated example the scanline 360 extends from the center of the array aperture between elements 8 and 9. This means that echo signals received by elements 8 and 9 will be in phase, and can be combined. Likewise, echoes received by paired elements 7 and 10, paired elements 6 and 11, and paired elements 5 and 12 can also be combined. Thus, following the first transmitted pulse, echoes received by elements 1–16 are delayed by the eight delay FIFOs and summed by the summing circuit 320. This half aperture is then stored for receipt of the other half aperture.

Another acoustic pulse is transmitted by all 32 elements of the aperture. After this second pulse, the receive muxes now connect echoes from elements 25–32 and 17–24 to the beamformer. By virtue of the folded aperture symmetry the echoes from element 32 are paired with echoes from element 17 and the two are combined. Likewise, echoes from element 31 are paired with echoes from element 18, and so forth, out to the most lateral paired elements 25 and 24.

The sixteen received echoes, paired to eight signals by the folded aperture, are appropriately delayed by the eight delay FIFOs and summed to form a second half aperture of the scanline. The two halves of the aperture are now summed as a function of the location of the echo components along the scanline of the two sequences. Thus, the complete aperture has been formed by combining the separate receptions of echoes from the inner sixteen elements of the aperture, then from the outer sixteen elements. A precisely beamformed synthetic aperture signal is produced by maintaining identical conditions of TGC control during both reception intervals. The dynamic weighting and dynamic focusing affect the two reception sequences differently by reason of the differing aperture locations of the receiving elements during the two sequences. The delays applied by the FIFOs during the two sequences will be different by reason of the differing locations across the aperture of the receiving elements from one sequence to the next.

Figure 8:
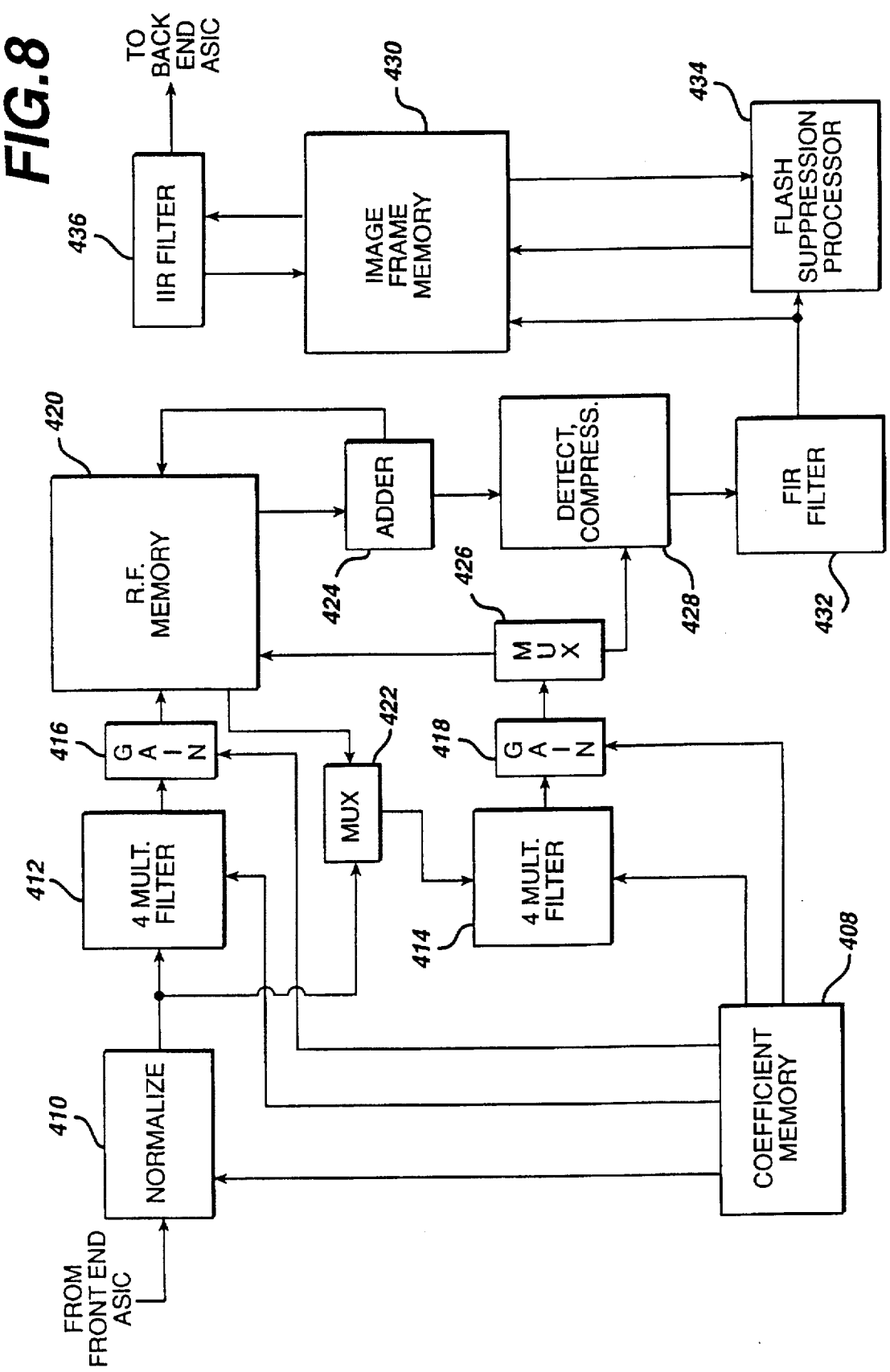
FIG. 8 is a block diagram of the digital signal processing ASIC of the ultrasound system of FIG. 1.

Referring to FIG. 8, a block diagram of the digital signal processing ASIC 40 is shown. Scanline signals from the front end ASIC 30 are received by a normalization circuit, where they are multiplied by a variable coefficient supplied by coefficient memory 408 to normalize the received signals for aperture variation. When the transducer is receiving signals along the scanline from shallow depths, a relatively small aperture, such as four or eight transducer elements, is used to receive echo signals. As the reception depth along the scanline increases, the aperture is incrementally increased so that the full 32 element aperture is used at maximum depths. The normalization circuit will multiply the received scanline signals by appropriate coefficients over the range of aperture variation, such as factors of four or eight, to normalize the signals for this aperture variation effect.

Figure 11:
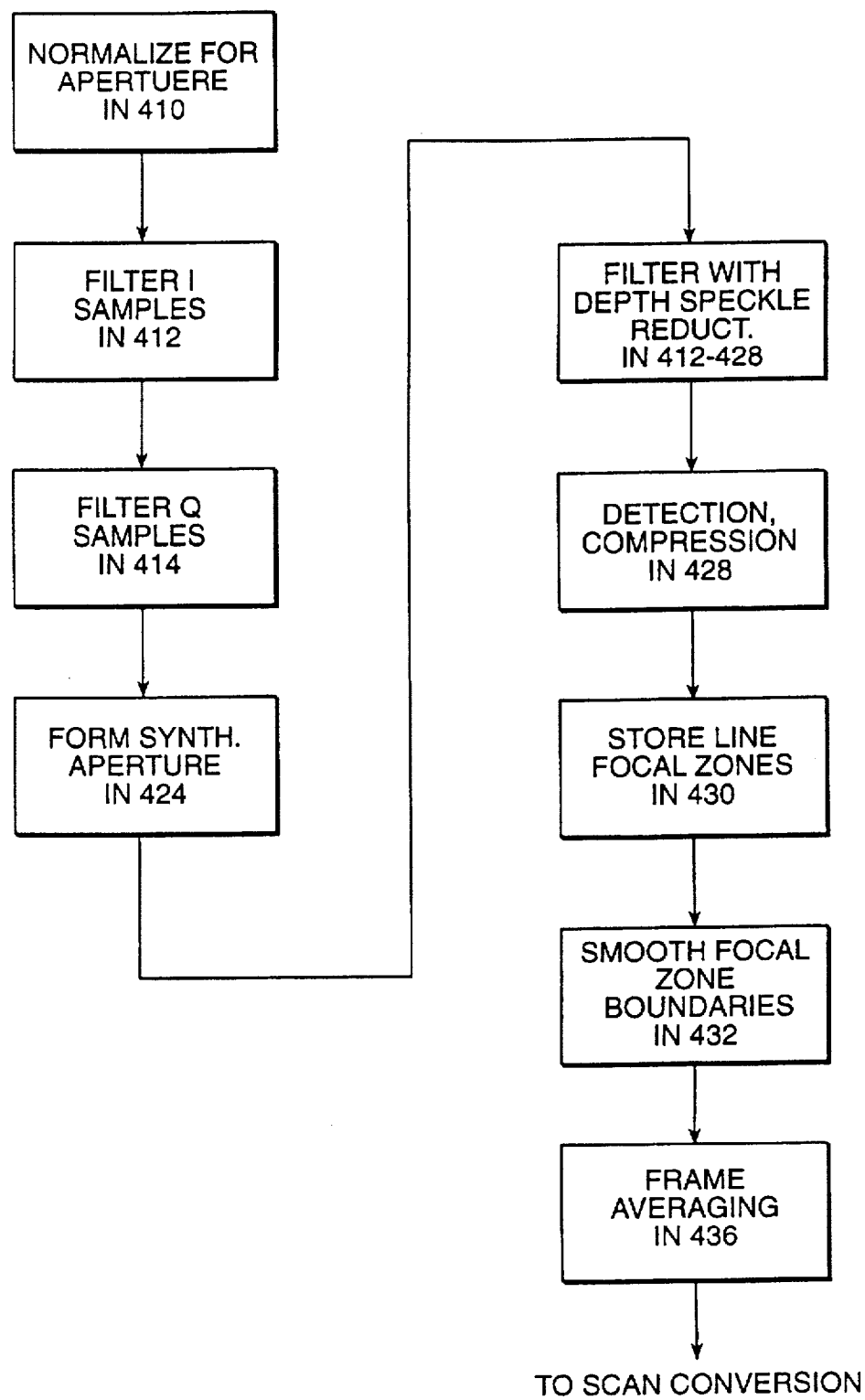
FIG. 11 is a flowchart of B mode processing by the digital signal processing ASIC.

When the ultrasound system is operated in the B mode to form a structural image of tissue and organs, the digital signal processor is operated as shown by the flowchart of FIG. 11. The normalized echo signals follow two paths in FIG. 8, one of which is coupled to a four multiplier filter 412 and the other of which is coupled by a multiplexer 422 to a second four multiplier filter 414. Each multiplier filter includes a multiplier and an accumulator which operate as an FIR (finite impulse response) filter. Scanline echo signals are shifted sequentially into a multiplier, multiplied by coefficients supplied by the coefficient memory 408, and the products are accumulated in the accumulator at the output of the multiplier. The coefficients for the filter 412 are chosen to multiply the echo signals by a cosine function and the coefficients for the filter 414 are chosen to multiply the echo signals by a sine function, preparatory for I and Q quadrature signal detection. The four multiplier filters produce accumulated signals at a rate which is less than the input rate to the multipliers, thereby performing decimation band pass filtering. When the signal bandwidth exceeds the display bandwidth of the display monitor, the image lines will flicker due to an aliasing condition. The decimation filtering is designed to reduce the signal bandwidth as well as the data rate to match the display bandwidth of the monitor. By applying a succession of input signals and coefficients to a multiplier and accumulating intermediate products, the effective length of the filter can be increased. For instance, input signals 1–8 can be sequentially weighted by the fourth multiplier and the products accumulated in the fourth accumulator; input signals 3–10 can be weighted by the third multiplier and the products accumulated in the third accumulator; input signals 5–12 can be weighted by the second multiplier and the products accumulated in the second accumulator; and input signals 7–14 can be weighted by the first multiplier and the products accumulated in the first accumulator. The data rate has thereby been decimated by two, and each multiplier and accumulator is effectively operated as an eight tap filter. Thus it is seen that the effective number of taps of the filer is a product of the number of multipliers (four in this example) and the decimation rate (two in this example).

Additionally, this filter reduces r.f. noise and quantization noise through its bandwidth limiting effects. I and Q echo signal samples are produced at the outputs of filters 412 and 414, amplified if desired by the multipliers of gain stages 416 and 418, then stored in the r.f. memory 420. The Q samples are coupled to the r.f. memory by a multiplexer 426.

When a synthetic aperture image is to be formed, the I and Q samples from the scanline of the first half of the aperture (see the discussion of FIG. 7 above) are stored in the r.f. memory until the I and Q samples from the other half of the aperture are received. As the samples from the second half of the aperture are received, they are combined with their spatially corresponding counterparts by an adder 424. The size of this memory is kept to a minimum by storing the aperture signals after decimation filtering, which reduces the size of the memory required to store the scanline signal samples.

After the I and Q samples for the full aperture have been formed, the echo samples are coupled from the adder 424 to a detection and compression circuit 428. This circuit includes two shift registers and a multiplier arranged to form a CORDIC processor for performing envelope detection of the form $(I^2+Q^2)^{1/2}$. See, for instance, "The CORDIC Trigonometric Computing Technique, by J. E. Volder, *IRE Trans. on Elect. Computers*, (Sept. 1959). The detected signal is compressed and scaled to map the detected signals to a desired range of display gray levels.

Following detection and compression mapping, the grayscale signals are lowpass filtered in an FIR filter 432, then stored in an image frame memory 430. If the selected scanning mode utilizes a single transmit focal point, the grayscale signals are transmitted to the back end ASIC 50 for scan conversion. Prior to leaving the ASIC 40, the greyscale signals can be frame averaged by an infinite impulse response (IIR) filter 436 which utilizes image frame memory 430 as a frame buffer and incorporates one multiplier and two adders to perform frame to frame averaging of the form $$F_{out}=(1-\alpha)F_{out-1}+\alpha F_{new}=F_{out-1}\alpha(F_{new}-F_{out-1})$$

where the multiplier coefficient is $\alpha$. If the coefficient is a binary number (e.g., 0.5, 0.25, 0.125) $F_{out}$ can be obtained with an add-shift-add operation.

If multiple focal zones are used, each received scanline segment is stored in the r.f. memory 420 until scanline segments from the entire display depth have been received. Preferably the scanline segments for one complete focal zone are acquired before transmitting and receiving segments from another focal zone. When all segments for a scanline have been acquired, each complete scanline is then read out of the memory and filtered by the FIR filter 432, which smoothes the boundaries between the segments for a more pleasing, artifact-free image.

If both multiple zone focusing and synthetic aperture are used, the scanline segments of both halves of the aperture are received over the full focal zone and assembled in the r.f memory 420. Corresponding scanline segments are then received from other focal zones and joined with the segments from the first received focal zone. The completed scanlines are then filtered by FIR filter 432 to smooth the boundaries between segments.

The user may choose to process the grayscale image with certain image enhancement features, such as depth dependent filtering or speckle reduction such as the frequency compounding technique described in U.S. Pat. No. 4,561,019. These optional processing techniques necessitate the use of the filters 412 and 414 for separate bandpass filtering of the scanline signals and absolute value detection rather than quadrature detection. In the case of depth dependent filtering the received echo signals are multiplied by cosine functions in both of filters 412 and 414, but with coefficients chosen so that one filter produces output signals in a high passband and the other produces output signals in a low passband. The output signals produced by the two filters are of the form $I_1=h_1(t)\cos\omega_H t$ and $I_2=h_2(t)\cos\omega_L t$. These two output signals are amplified in gain stages 416 and 418 by complementary time varying gain control functions. The high frequency passband signals $I_1$ are initially amplified strongly, then the gain is decreased as echo signals are received from increasing depths along the scanline. In a complementary manner the low frequency passband signals $I_2$ are initially at a low level, then amplified in an increasing manner with depth as the high frequency gain is rolled off. Thus, signals at shallow depths will exhibit a relatively high passband, and signals from greater depths will pass through a relatively lower passband which reduces high frequency noise at the greater depths. Detection in the CORDIC processor of circuit 428 is performed by absolute value detection by squaring $I_1$ and $I_2$, then summing the results. Following summation the signals are log compressed to the desired grayscale mapping characteristic. Alternatively, the signals passed by the separate passbands are summed by the adder 424, then detected by absolute value detection in the detection and compression circuitry 428 and mapped.

The same processors can be used to provide speckle reduction by frequency compounding. The coefficients of one of the filters 412,414 are chosen to filter the received signals by a high frequency passband, and the coefficients of the other filter are chosen to filter the received signals by a contiguous low frequency passband. The coefficients of the gain stages 416,418 are chosen to equalize the responses of the two passbands. The signals of the high and low passbands are coupled to the detection and compression circuitry where the passbands are separately detected through absolute value detection as described above, then the detected signals are log compressed to the desired grayscale mapping characteristic and summed on a spatial basis.

Figure 12:
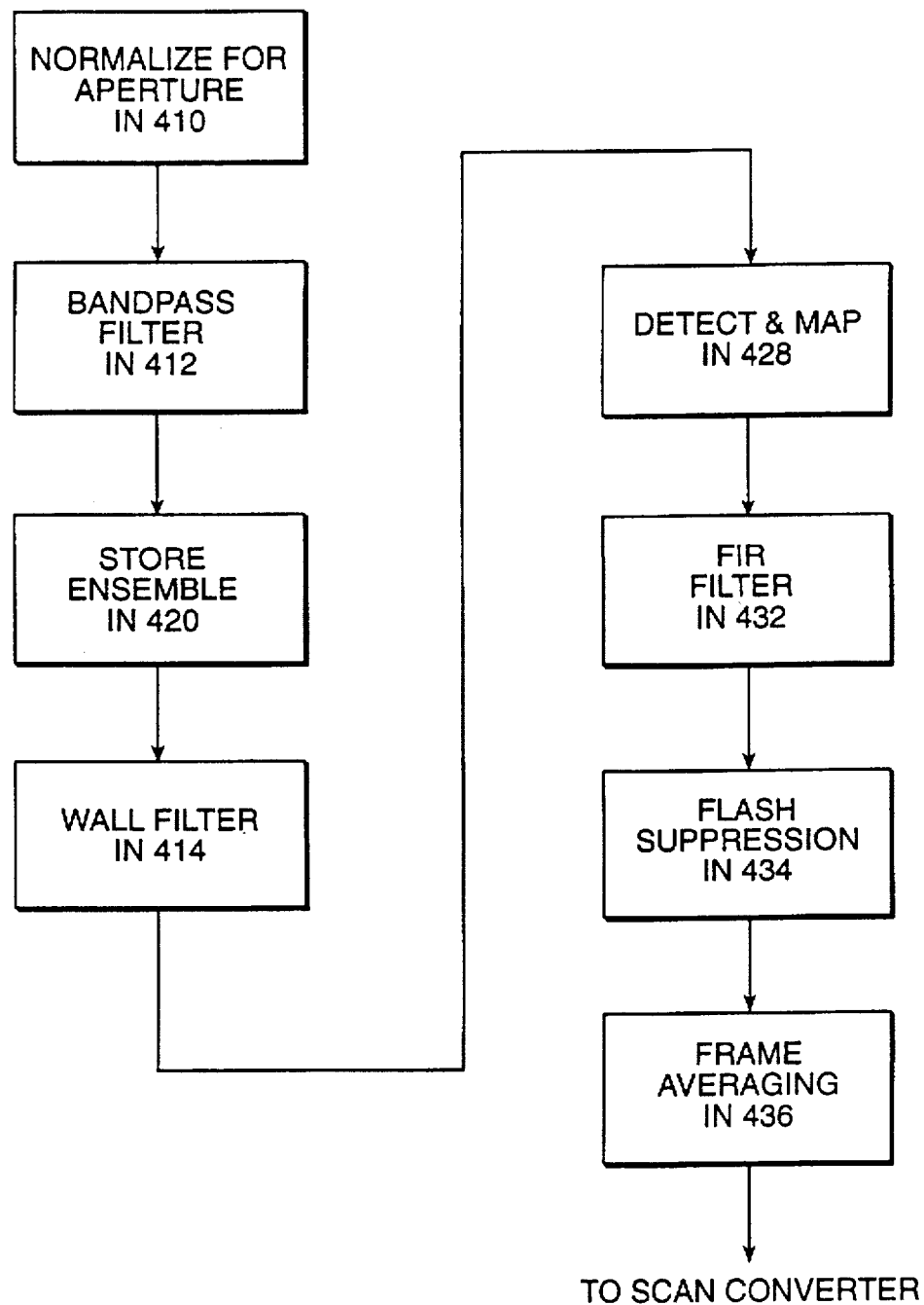
FIG. 12 is a flowchart of Doppler processing by the digital signal processing ASIC.

The processing of Doppler echo signals for power Doppler (CPA) display is shown in FIG. 8 together with the flowchart of FIG. 12. Each scanline vector is scanned repetitively, for instance eight times, to assemble an ensemble of Doppler information along the vector. Each received scanline of echo signals is normalized by the normalization circuit 410 and undergoes decimation band pass filtering in the filter 412. Each scanline of the ensemble is stored in the r.f. memory 420 until a complete ensemble has been accumulated. The scanlines of each ensemble are coupled by the multiplexer 422 to the four multiplier filter 414, which performs wall filtering and Doppler power estimation through matrix filtering. Wall filtering is performed by selection of appropriate multiplier coefficients and the matrix filtering is of the form $$\begin{bmatrix} y_1 \\ y_2 \\ y_3 \\ \cdot \\ \cdot \\ \cdot \\ y_n \end{bmatrix} = \begin{bmatrix} a_{11} & a_{12} & a_{13} & \cdots & a_{1n} \\ b_{11} & b_{12} & b_{13} & \cdots & b_{1n} \\ c_{11} & c_{12} & c_{13} & \cdots & c_{1n} \\ \cdot & \cdot & \cdot & & \cdot \\ \cdot & \cdot & \cdot & & \cdot \\ \cdot & \cdot & \cdot & & \cdot \\ z_{11} & z_{12} & z_{13} & \cdots & z_{1n} \end{bmatrix} \begin{bmatrix} x_1 \\ x_2 \\ x_3 \\ \cdot \\ \cdot \\ \cdot \\ x_n \end{bmatrix}$$

where $x_1 \ldots x_n$ are spatially aligned signals from the ensemble of scanlines and $y_1 \ldots y_n$ are output Doppler values. In a preferred embodiment a four multiplier filter is used for matrix filtering, and the filtering is performed sequentially and incrementally. Intermediate products are accumulated as described above, thereby extending the filter length. For example, in processing the above matrix with a four multiplier filter, the intermediate products $a_{11}x_1+a_{12}x_2+a_{13}x_3+a_{14}x_4$ are formed initially and summed in the accumulator. Then products $a_{15}x_5+a_{16}x_6+a_{17}x_7+a_{18}x_8$ are formed by the multipliers and summed in the accumulator with the previously computed intermediate products. By accumulating intermediate products in this manner the four multipliers and accumulator can be extended to a filter of any desired length, restricted only by the maximum processing time available. The Doppler values are coupled to the detection and compression circuitry 428 through the gain stage 418 and the multiplexer 426, where the Doppler signal amplitude at each echo location along the scanline is detected through absolute value detection of the form $$y = \sum_{n}^{1-n} y_n^2$$

The Doppler values y are then compressed and scaled using the CORDIC processor of the detection and compression circuitry 428.

Figure 9:
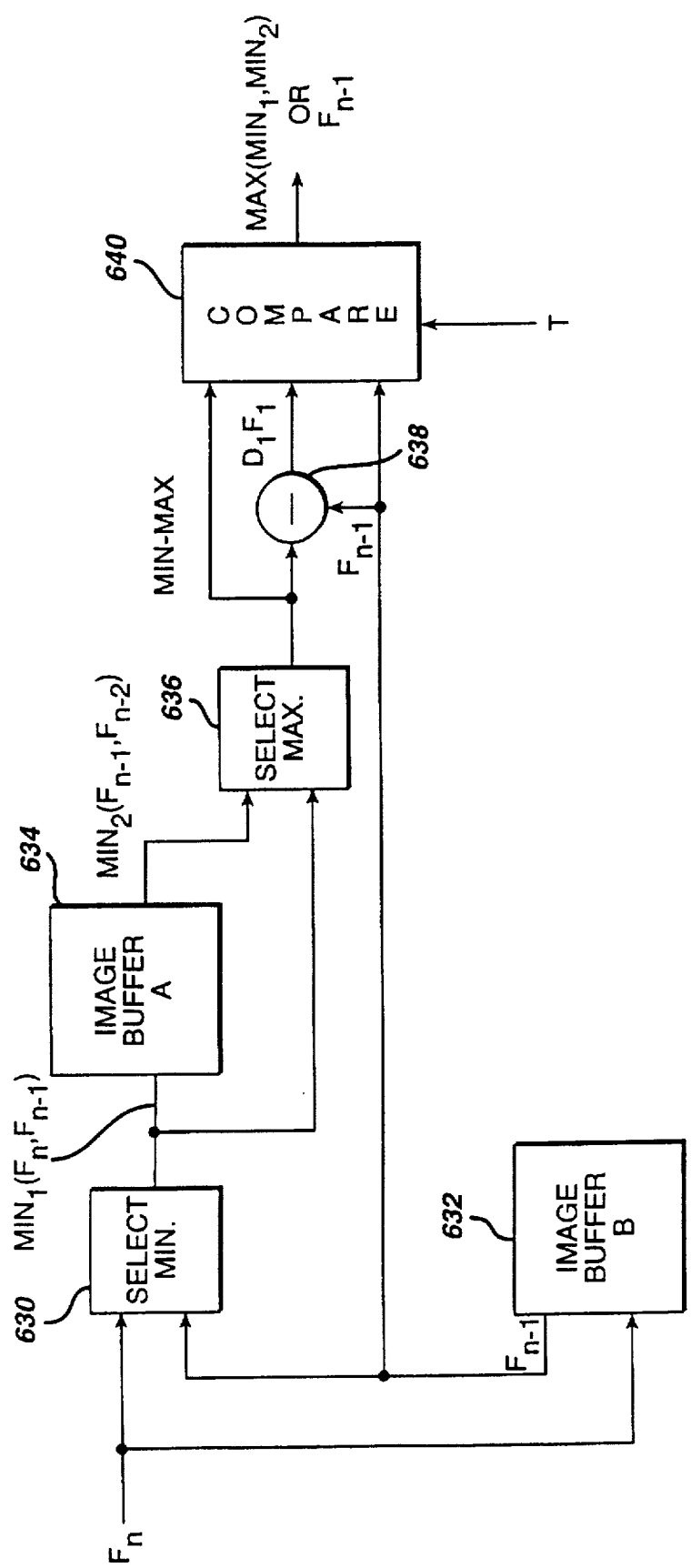
FIG. 9 illustrates a min-max filter for flash suppression.

Once the Doppler signal amplitude values have been detected and filtered by FIR filter 432, the resulting values are spatially stored and image clutter is removed by a flash suppression processor 434, which eliminates large frame to frame variations in the displayed signals. A preferred technique for flash suppression processing is min-max filtering as shown in the detailed diagram of the flash suppression processor of FIG. 9. Min-max filtering, a class of morphological filtering, is performed on temporal signals from a sequence of Doppler image frames. FIG. 9 illustrates the processing of temporal data at a particular sample volume location, with the frame being processed identified as frame $F_{n-1}$. When the Doppler signal from a new frame $F_n$ is received, it is compared with the value of the previous frame $F_{n-1}$ and the minimum value of the two is selected by a minimum value selector 630. This minimum value $Min_1$ is expressed as $Min_1(F_n,F_{n-1})$. The minimum value $Min_1$ is compared with the previously selected minimum value $Min_2(F_{n-1},F_{n-2})$ which is stored in an image buffer A, and the maximum of the two values is selected by a maximum value selector 636. The selector 636 therefore selects the maximum of two minimum values, expressed as a min-max value. The min-max value is subtracted from the Doppler signal value of the current frame $F_{n-1}$ by a subtractor 638. A comparator 640 compares this difference against a signal excursion threshold T. If the difference exceed the threshold T, the comparator 640 produces the min-max value for the Doppler signal value of the current frame. If the difference does not exceed the threshold T, the current frame value $F_{n-1}$ is used. When this selection has been made, the $Min_1$ value is latched into the image buffer A in place of the previous $Min_2$ value, new frame value $F_n$ is latched into image buffer B, and the process continues for the other sample volume locations in the current frame, and then the following frame.

This processing may be understood by considering the following sequence (1) of Doppler signal values which are received over time from a given sample volume location:

$$0, 1, 2, 15, 7, 4, 8, 5, 7, 25, 8 \qquad (1)$$

Where the first value 0 is of frame $F_n$ and the second value 1 is of frame $F_{n-1}$. When pairs of consecutive values are examined for the minimum of the two, the following sequence (2) of minimum values results:

$$0, 1, 2, 15, 7, 4, 8, 5, 7, 25, 8 \qquad (1)$$

$$0, 1, 2, 7, 4, 4, 5, 5, 7, 8 \qquad (2)$$

This shows that the minimum of the first two values of the sequence (1), 0 and 1, have a minimum value of 0 which is the first value in the sequence (2). The second and third values of sequence (1), 1 and 2, have a minimum value of 1, the second value in the sequence 2. The third and fourth values of sequence (1), 2 and 15, have a minimum value of 2, the third value in the minimum value sequence (2). Sequential values in the minimum value sequence (2) are then compared to determine the maximum of the two as shown by the min-max sequence (3):

$$0, 1, 2, 15, 7, 4, 8, 5, 7, 25, 8 \qquad (1)$$

$$0, 1, 2, 7, 4, 4, 5, 5, 7, 8 \qquad (2)$$

$$1, 2, 7, 7, 4, 5, 5, 7, 8 \qquad (3)$$

Thus it is seen that the first two values of the minimum value sequence, 0 and 1, have a maximum value of 1, the first value in the min-max sequence (3). The minimum values 1 and 2 have a maximum value of 2, the minimum values 2 and 7 have a maximum value of 7, and so forth.

From the min-max sequence (3) it is seen that the sudden excursions of the fourth, seventh and tenth values of the first sequence, 15, 8, and 25, have been eliminated in the min-max sequence. In the illustrated embodiment the difference between the current value and the min-max value is compared to a threshold and the min-max value used if the difference exceeds the threshold. In this numerical example this difference is the difference between the first and third sequences. If the threshold used is 6, for example, each of the excursions of 15 and 25 would be replaced by min-max values in the processor output. The original values would be used in all other cases.

Figure 10A:
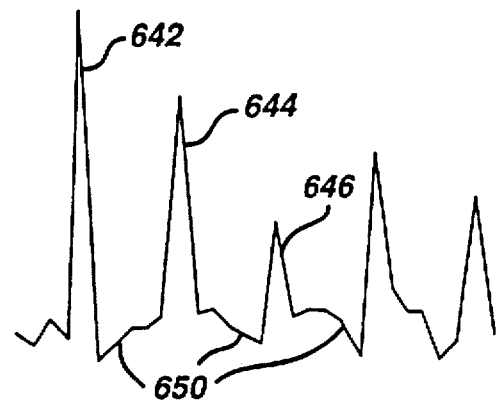
FIG. 10a–10c are waveforms illustrating the operation of the flash suppression processor.
Figure 10B:
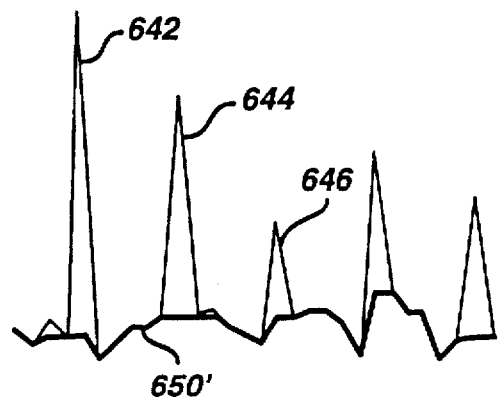
Figure 10C:

Min-max processing as described above will follow the received Doppler signals for signal variations within expected ranges, but will substitute min-max values to smooth over sudden signal excursions, as shown in FIG. 10 FIG. 10a shows a sequence 650 of signal values at a given location in a Doppler image. The sequence 650 is contaminated by sudden excursions 642, 644, and 646, which are artifacts from flash (scanhead movement) or other noise sources. The min-max filter of FIG. 9 will substitute min-max values in place of these undesired excursions, as shown by the solid signal sequence 650 below the undesired excursions in FIG. 10b. With the undesired excursions replaced by min-max values, the signal level sequence 650 which is processed for display is as shown in FIG. 10c. A benefit of the min-max processor is that it is effective only for positive excursions. The local peaks and valleys which represent the local temporal variations of Doppler power are preserved by this filtering technique.

The image frame memory 430 is capable of storing either a gray scale frame or a power Doppler frame. Each frame can be temporally filtered by the IIR filter 436, which performs frame averaging on a point-by-point basis as described above. The temporally filtered image information is then provided to the back end ASIC 50 for scan conversion and display.

The sequences of operating the digital signal processing ASIC 40 for B mode (two dimensional) echo and Doppler processing, respectively, are outlined in the flowcharts of FIGS. 11 and 12, respectively. The number in each flowchart block of FIGS. 11 and 12 refers to the numbered processor in the ASIC block diagram of FIG. 8.

The image frame memory 430 of the digital signal processing ASIC shares a common architecture and implementation technology with the frame buffer memory of the back end ASIC discussed below. To take advantage of this commonality and the resultant efficiency in ASIC fabrication and density, the image frame memory 430 and its associated flash suppression processor 434 and IIR filter 436 can be located on the back end ASIC 50, thereby partitioning the digital signal processing ASIC and the back end ASIC at the output of FIR filter 432.

Figure 13:
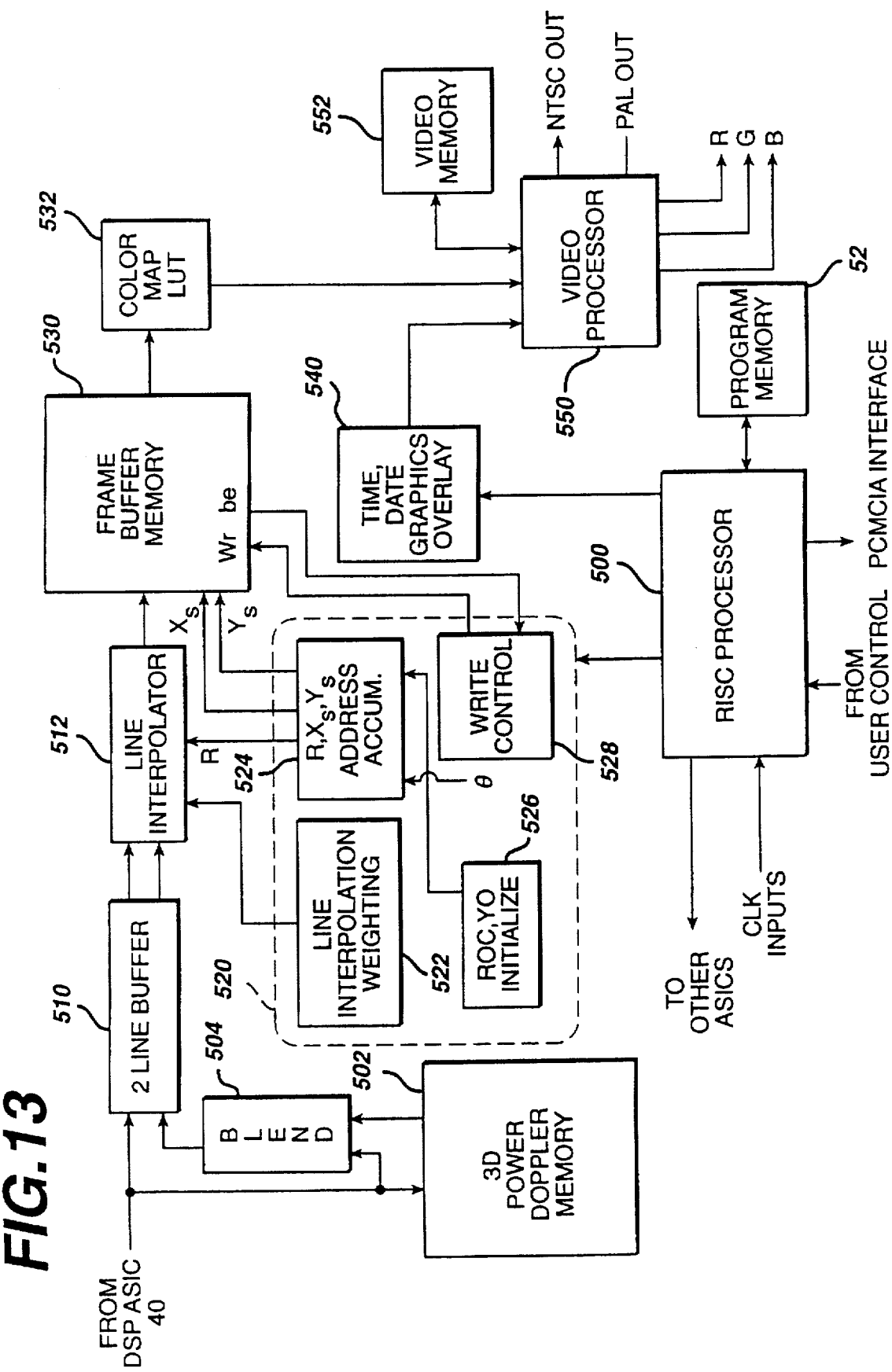
FIG. 13 is a block diagram of the back end ASIC of the ultrasound system of FIG. 1.
Figure 14:
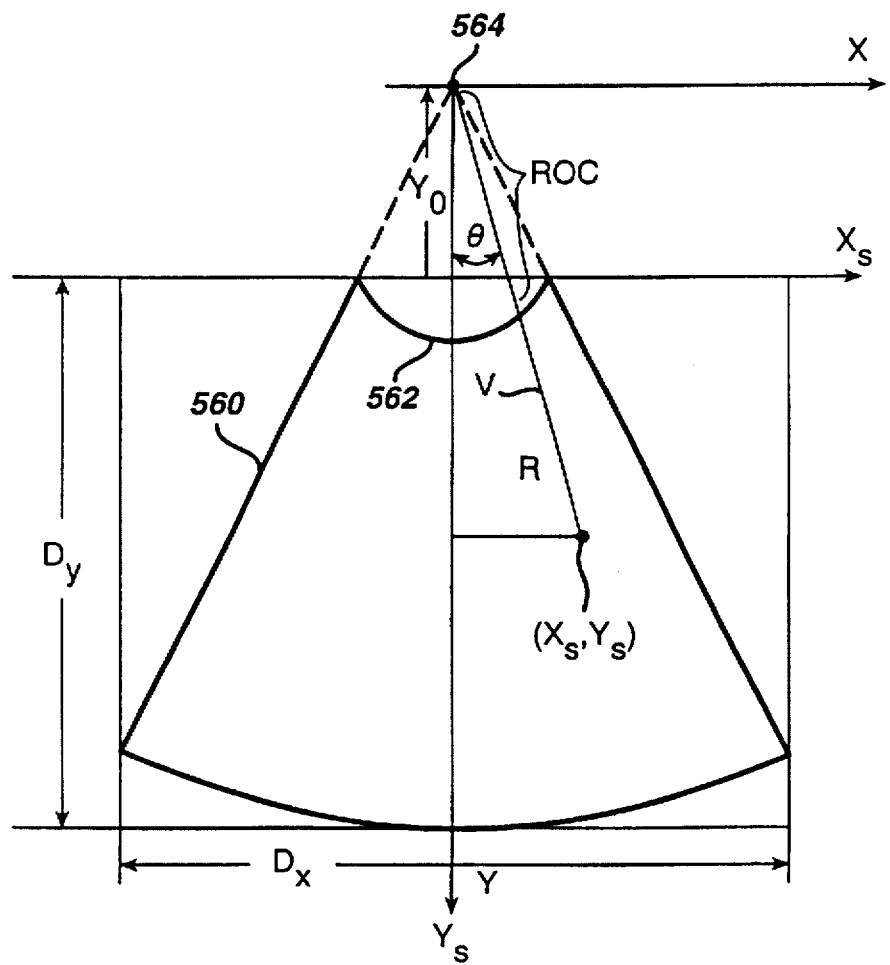
FIG. 14 illustrates R$\theta$ scan conversion in accordance with the present invention.

Referring to FIG. 13, the block diagram of the back end ASIC 50 is shown. Processed B mode scanlines produced by the digital signal processor ASIC 40 are coupled to a buffer 510 which stores two consecutive scanlines for scan conversion. In order to economize on the integrated circuit area, power requirements, and heat dissipation needed for the scan conversion function, a straightforward linear interpolation algorithm and simple conversion technique requiring only adders and accumulators for addressing are employed. In the case of the use of a curved array transducer 10 as shown in FIG. 1, the scanned sector 560 as shown in FIG. 14 is scan converted in the following manner. In FIG. 14 the radial scanlines of sector 560 are converted to the x,y coordinates of a frame buffer memory 530 of FIG. 13, the boundaries of which are defined as $D_x$ and $D_y$ in FIG. 14. The radial scanlines of the sector 560, one of which is shown at vector V, emanate from the virtual apex point 564. With a curved array there are no data points between the virtual apex and the skinline (transducer location) 562, although with a phased array scanhead the apex would be in the $D_x,D_y$ image area. In the case of a linear array there is no apex, and the parallel scanlines and interpolated lines are simply recorded into the frame buffer memory 530. The following example describes scan conversion of the most complex of the arrays for scan conversion, the curved array 10. From this example scan conversion with other array formats will be apparent.

In FIG. 14 the scanlines are defined by polar R,θ coordinates, which are to be converted to the $x_s,y_s$ coordinates of the display screen. The polar coordinates have an origin at apex point 564, whereas the screen coordinates have an origin (0,0) at the top center of the display area. The screen coordinate origin is offset from the apex by the distance $y_o$ in the y direction, and is at the top center of the $D_x,D_y$ image area. In the case of the curved array, there are no valid data points along the initial radius of curvature segment $R_{oc}$ of each vector V. Beyond the initial distance $R_{oc}$ (which is below the skinline 562) valid echo data exists and will be located to the proper address in the scan converter memory 530. The dot at the end of vector V in FIG. 14, for instance, has polar coordinates of R,θ which are to be converted to screen coordinates $x_s,y_s$ and located at that address of the scan converter memory.

Figure 15:
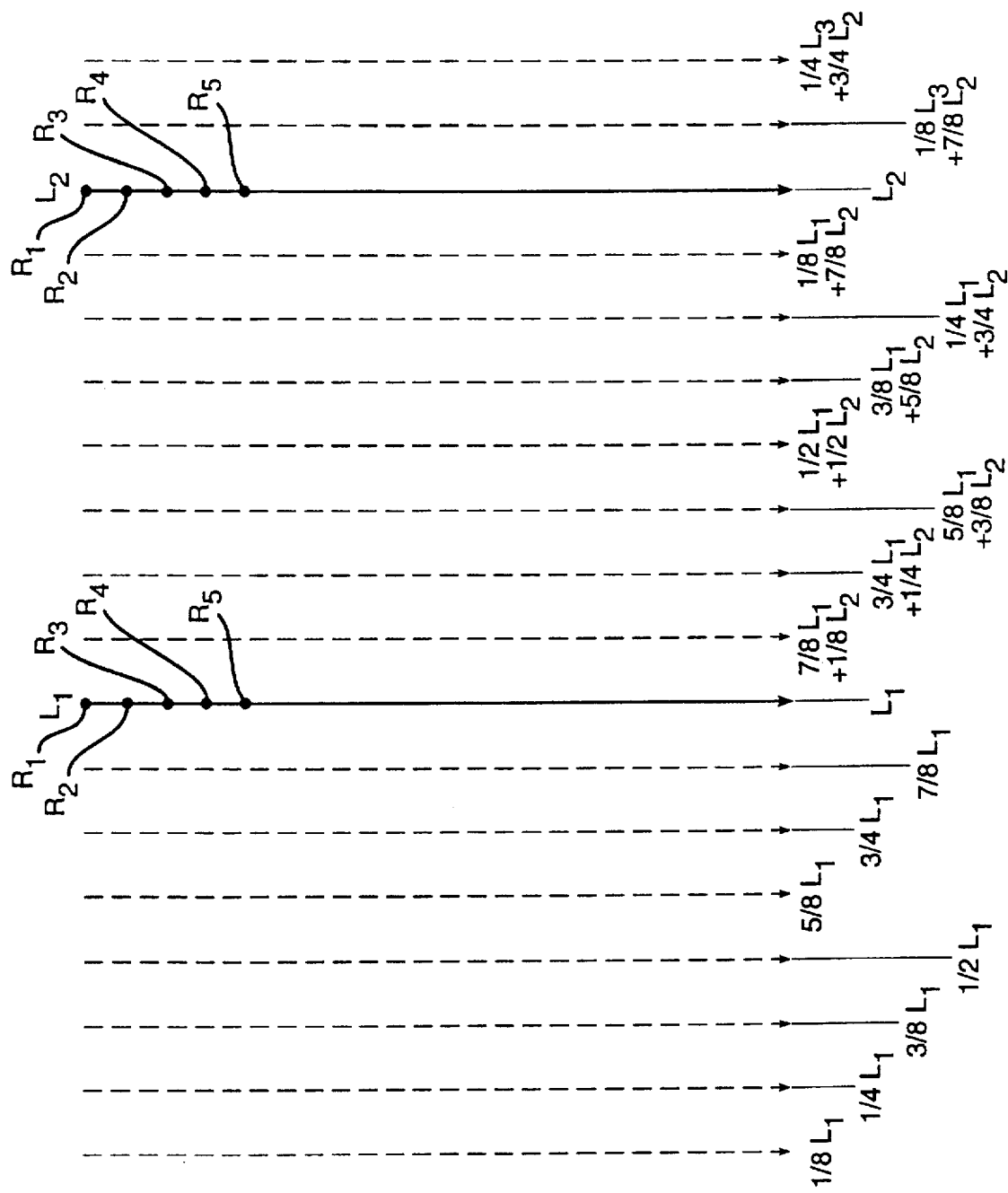
FIG. 15 illustrates scanline interpolation by the scan converter.

Prior to scan conversion the two scanlines stored in the two line buffer 510 are used to interpolate a number of interlineated scanlines. A linear interpolation scheme $\alpha L_1 + (1-\alpha)L_2$ as shown in FIG. 15 has been found to produce satisfactory results. The preferred implementation expression is $L_2 + \alpha(L_1 - L_2)$ which requires only a single multiplier. In the example of FIG. 15, seven scanlines are interpolated between each pair of received scanlines $L_1$ and $L_2$. The illustrated scanline $L_1$ is at the radial boundary of the sector 560. Interpolated scanlines radially outward from this boundary scanline (to the left in the drawing) are produced by weighting the data values on scanline $L_1$ by weights of ⅞, ¾, ⅝, ½, ⅜, ¼, and ⅛ as shown to the left of scanline $L_1$ in FIG. 15. Between scanline pairs the interpolated scanlines are weighted combinations of both $L_1$ and $L_2$, as shown by the weighted values of ⅞$L_1$+⅛$L_2$, ¾$L_1$+¼$L_2$ and so forth. Interpolation is done by taking a data value along the scanline such as $R_1$, weighting it by a weighting factor such as ⅞, then adding it to a complementary weighted, spatially corresponding data point $R_1$ from the next scanline. Interpolation in this manner proceeds down the scanline until finished, then the next scanline is interpolated. As interpolated scanlines are produced they are immediately placed in the frame buffer memory 530.

FIG. 13 shows the two line buffer 510 which holds the two scanlines $L_1$ and $L_2$ while the line interpolator 512 uses the buffered scanlines to produce interpolated scanlines. Weights for the interpolation process are provided by the line interpolation weighting store 522 of the scan conversion controller 520. When the intervening interpolated lines have been produced, the oldest scanline in the two line buffer 510 is replaced by a new adjacent scanline. Since the locations which store the two scanlines in the buffer 510 are updated alternately, the weights used for the retained scanline are simply used in the next interval in the reverse order. In FIG. 15 it is seen, for example, that scanline $L_2$ is weighted in the interval between lines $L_1$ and $L_2$ with weights increasing from ⅛ to ⅞. After line $L_1$ is replaced with the next line $L_3$, scanline $L_2$ is weighted in the reverse order, declining from ⅞ to ⅛ in the following interval. This avoids the need to move the retained scanline from one area to another in buffer 510; it is only necessary to replace the oldest scanline with a new one.

It follows that the received scanlines are passed through the line interpolator 512 without change at the appropriate times in the scanline sequence.

As scanlines are produced at the output of the line interpolator 512 their data values are scan converted to the storage locations in the frame buffer memory 530 in the following manner. The polar coordinates of the radial scanlines are related to the rectangular coordinates of the memory 530 by $$x = R \sin \theta$$

and $$y = R \cos \theta$$

where R is the radial distance along a vector extending at an angle θ with respect to the y axis in FIG. 14. Solving for R and then substituting the solution for R in the expression for x yields $$R = y/\cos \theta$$

and $$x = y \tan \theta$$

These expressions are used to increment values in the R, $x_s$, and $y_s$ accumulators to provide simple scan conversion addressing.

As the line interpolator begins outputting a scanline, the scanline data from selected R addresses along the scanline are stored in the frame buffer memory 530 at $x_s, y_s$ addresses. Data storage starts at the first row (y=1) of the memory area $D_x, D_y$, and proceeds sequentially down the rows of the memory. Thus, the $y_s$ accumulator simply accumulates integer values starting at 1. The R accumulator is initialized to a value of $y_o \cos \theta$, which offsets the first scanline address from the apex of the scanlines to the sample of the scanline which is aligned with the first row of the memory in FIG. 14. The $x_s$ address for the memory 530 is initialized to a value of $y_o \tan \theta$, the point along the first row of the memory which intersects the R,θ vector V in FIG. 14. The $y_o$ values for the initialization values are provided by an initialization storage device 526.

From these starting address values the R accumulator which addresses the line interpolator 512 is incremented by a constant 1/cosθ to sequentially step from one R,θ scanline value which is to be stored to the next. The $y_s$ accumulator which addresses the frame buffer memory 530 is incremented by integer values and the $x_s$ accumulator for the memory 530 is incremented by a constant 1/tanθ to step to each new storage address of the frame buffer memory.

Two further steps are involved in the scan conversion process. One is a check of the R addresses against a constant for the scanline which accounts for the radius of curvature $R_{oc}$ of the transducer array. As FIG. 14 shows, the boundary scanlines at the outermost periphery of the sector 560 start from the top row of the $D_x, D_y$ display area, but all other scanlines of the curved array start below the top due to the curvature of the array. To account for this, an offset due to the curvature is calculated for each scanline in units of the R address. As the R address accumulator produces its initial R addresses they are compared with the calculated $R_{oc}$ offset. R addresses produced by the R address accumulator are ignored until the first R address which exceeds $R_{oc}$, from which point data values of the scanline are stored in the memory 530.

Another step which is performed before scanline data values are written into the selected address locations of the memory 530 is to check whether a data value was previously written to the selected address location. A one bit map of bits $b_e$ corresponding to address locations in the frame buffer memory is used as each image frame is scan converted. When a new data value is written to a location in memory, the corresponding bit $b_e$ for that address location is set, indicating that a data value has been entered into memory for that frame. If scan conversion of another scanline during that frame addresses the same memory location, the $b_e$ bit tells the write controller 528 that a data value has already been entered at that location for that frame. This will cause the write controller to cancel entry of the new data value, or overwrite the previously stored data value, depending upon the protocol chosen by the user or the scan controller designer. The scan converter may utilize a protocol which replaces previously entered data values with new ones, or only enters the first data value and ignores all later values. Another protocol is to overwrite old values with new ones as scanlines proceed from the periphery to the center of the image, then to enter the first value found and reject subsequent values for scanlines proceeding from the center of the image to the periphery. In a preferred embodiment the protocol is simply to enter the first data value for each memory location, and ignore subsequent attempts to overwrite the location with new data.

When all scanlines have been written into the memory 530, the map of $b_e$ bits contains all ones. During the next image frame these bits are inverted to zeroes as data values for the new frame are written to the storage locations of the memory. Thus, there is no need to reset the $b_e$ bit map between frames; complementary $b_e$ bit values are used to map data entries for successive image frames.

Figure 16:
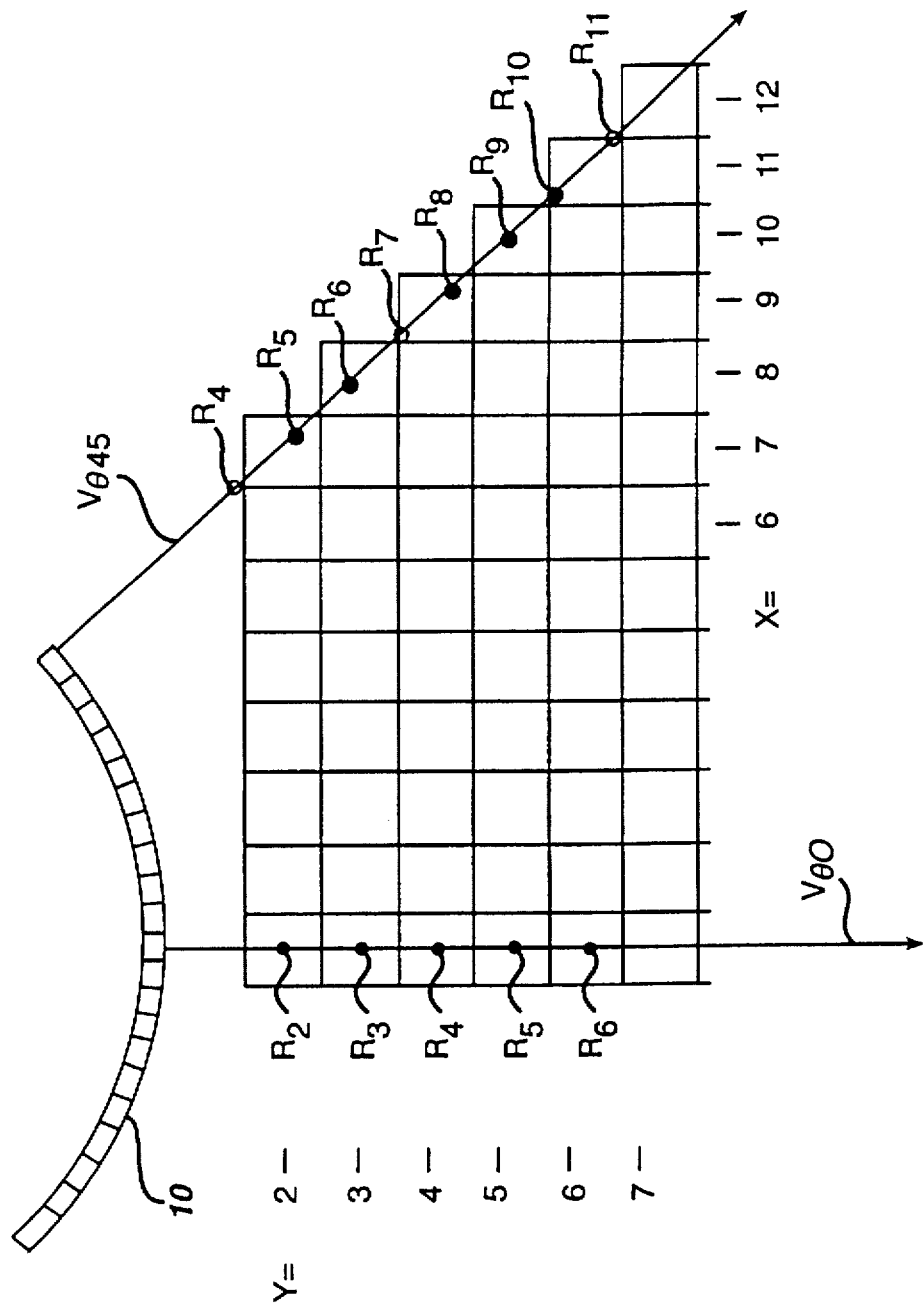
FIG. 16 is a further illustration of scan conversion in accordance with the present invention.

The operation of the scan conversion process is illustrated in FIG. 16, where two scanline vectors $V_\theta$ and $V_{\theta 45}$ are seen extending from the curved transducer array 10. A matrix of blocks is shown to spatially represent memory locations in the scan converter buffer memory 530. The scanline $V_{\theta 0}$ extends from the center of the array and is orthogonal to the memory matrix and is identified as extending at an angle $\theta=0°$. When the scanline data samples have been bandlimited in the digital signal processing ASIC 40 as described above, the detected samples along the scanline vector will fall sequentially into consecutive memory locations in a column of the memory 530. This is shown by consecutive scanline R values $R_2$, $R_3$, $R_4$, $R_5$ and $R_6$ at consecutive y addresses 2 through 6. If the scanline data has not been bandlimited to match the bandwidth of the display, a number of intermediate samples will be skipped as the R address accumulator 524 is incremented from row to row. The scanline data can thus be scaled during scan conversion if it has not been scaled earlier in its processing.

The other scanline at vector $V_{\theta 45}$ extends at an angle of 45° with respect to the first vector. At this angulation it is seen that there are more samples than blocks (locations) in the memory matrix along the scanline vector. The rows of the memory matrix are addressed in integer values of y from 2 through 6 over the scanline interval shown in the drawing. The x addresses of the memory are incremented by the constant of ytan$\theta$ for each row y, using the tangent of the scanline angle, tan 45°. This results in a sequence of x addresses of 7 through 11 for the portion of the $V_{\theta 45}$ scanline shown in the drawing. The R addresses along the scanline are incremented by the constant y/cos$\theta$ as described above, and fractional amounts are truncated to yield the selected R addresses shown by the solid circles. It is seen that the $R_4$ value is not used, and R values of $R_5$ and $R_6$ are stored at x,y addresses of 7,2 and 8,3. The $R_7$ value is skipped and the next three R values, $R_8$, $R_9$, and $R_{10}$ are stored in rows 4, 5, and 6. The next R value, $R_{11}$, is skipped before a scanline value is stored in the next row. It has been found that truncation of the fractional portion of the R value will choose the most accurate scanline R value, that is, within a one pixel tolerance, for each location in the scan converter memory.

Each memory location in the frame buffer memory 530 stores a data value from a received or interpolated ultrasonic scanline and two additional bits. Of these two additional bits, one is set to identify the stored data value as either a black and white or a color data value; a 0 identifies the data value as a black and white pixel, and a 1 identifies the data value as a color pixel. When this bit is set for a color pixel, the data value at the pixel accesses a color map look-up table 532, which selects the proper red (R), green (G), and blue (B) signal values for display. A 0 value results in display of the data value as a gray level pixel. The second additional bit, as described above, is the $b_e$ bit which maps the entries of data values into memory for each image frame. The $b_e$ bit is read by the write control circuit 528 to determine whether a new data value is to be written to memory in accordance with the protocol used by the scan converter.

The scan converted frame in buffer memory 530 is read from the memory after the frame has been assembled. Color pixels look up R, G, and B values in the color map look-up table 532, which are then passed to a video processor 550.

Grayscale pixels are passed directly to the video processor. In the video processor, the ultrasonic image is overlaid with graphics from the graphics overlay buffer 540. This graphic information can comprise time, date, patient identification, scale markers, Doppler window outlines, cursors, and other graphical information useful to the user. The ultrasound image and its graphical information may then be produced as an output signal for a display. A variety of output signal formats are possible, including NTSC video format, PAL format, or RGB format. The output signals are produced at a digital to analog converter output of the video processor 550 and may be baseband or modulated carrier signals. The signals may drive the unit's own LCD display 60, or are produced at an output terminal for a separate, external monitor. The unit includes a video memory 552 for Cineloop storage and replay of a real time image sequence designated by the user for storage and replay.

Figure 18:
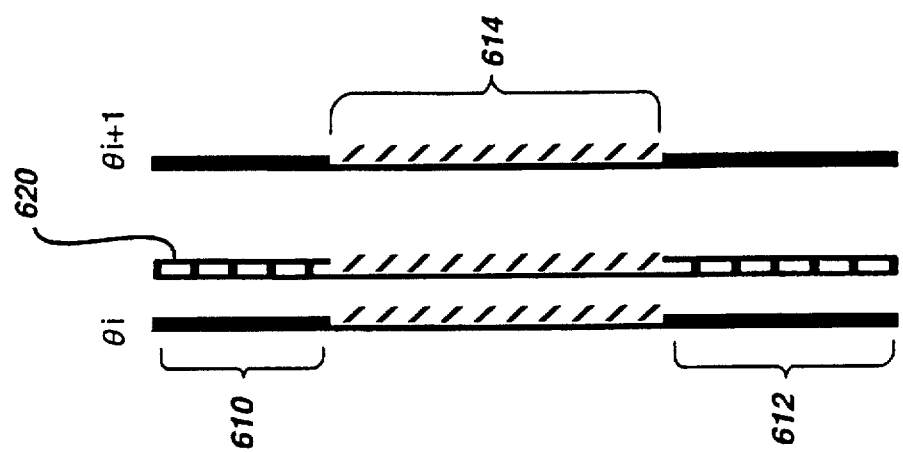
FIG. 18 illustrates combined B mode and Doppler scanlines.
Figure 17A:
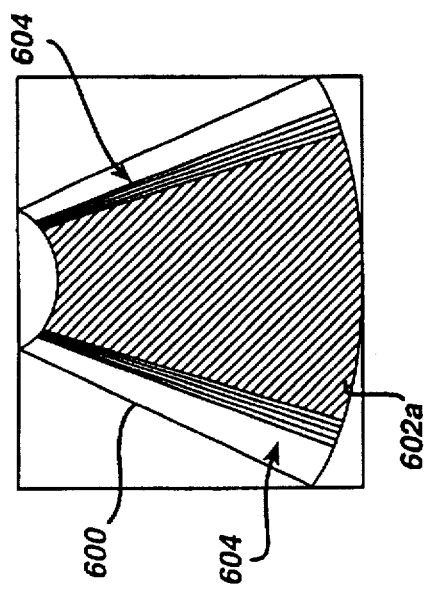
FIG. 17a and 17b illustrate combined B mode and Doppler images.
Figure 17B:
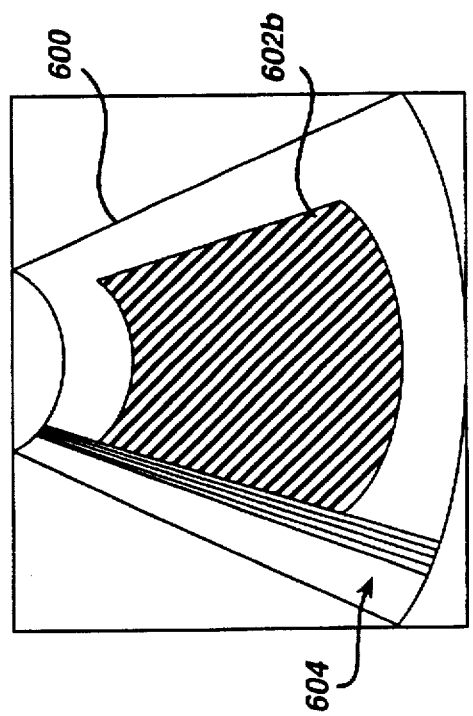

The ultrasound image produced by the handheld system may be a B mode grayscale image, a power Doppler image, a combination of grayscale and power Doppler image information, or a three dimensional power Doppler image. When a combined grayscale and power Doppler image is produced, the user will designate a subsector window within the full sector over which power Doppler signals will be gathered and displayed. Such a subsector 602 is shown as a shaded subsector in the sector 600 of FIG. 17. The subsector 602a may extend completely from the top to the bottom of the sector 600, as shown in FIG. 17a, in which case the subsector scanlines will be power Doppler lines, and the scanlines on either side of the subsector 602a, such as the groups of lines indicated at 604, are produced as grayscale lines. In the preferred embodiment the height of the power Doppler subsector window is also controllable by the user to allow the subsector to be bordered on all sides by grayscale image information, as shown by subsector 602b in FIG. 17b. Moreover, the power Doppler information is blended with B mode grayscale information over the area of the subsector window. This is shown in FIG. 18 with reference to FIGURE 13. As scanlines of power Doppler information over the subsector area are received, the power Doppler signals are stored in a 3D power Doppler memory 502. When scanlines of B mode data are received which overlap the subsector, those scanlines are applied to a blending circuit 504. The spatially coincident power Doppler signals are applied to the blending circuit at the same time, and scanline data which is a blend of both power Doppler and grayscale information is produced by blending the data together. Two such received and blended scanlines are shown in FIG. 18 as scanlines $\theta_i$ and $\theta_{i+1}$. As these lines shown, the top (near field) portion 610 of each line and the lower (far field) portion 612 of each line comprises only grayscale data. In the intermediate portion 614 of each received line, grayscale and power Doppler information is blended together. For instance, if power Doppler information is to be displayed in a solid red color and grayscale information is to be displayed as different brightness levels, the blending of these two types of information could result in a bright red color, a dimly red color, a light pink color, or other combination of a measured variation of the color red and a level of brightness. As received scanline information is blended, the blended lines are provided to the two line buffer 510 for interpolation of intermediate scanlines and scan conversion. Interpolated lines such as interpolated scanline 620 are produced intermediate the two received scanlines in the manner shown in FIG. 15. Thus, the blended region of each line, when the lines are scan converted and displayed adjacent to each other, will convey information on both the blood flow and the tissue structure of the region of the body depicted in the power Doppler subsector 602.

One image boundary refinement is worth noting. To correctly fill the image area when the Doppler scanline information is overlaid on the grayscale scanline information, the beginning of the Doppler information area should be overlaid on top of the last grayscale line. As the Doppler scanline area is completed the last Doppler scanline is overlaid by the first scanline of the remainder of the grayscale portion of the image.

The handheld ultrasound system of the present invention is also capable of presenting power Doppler images in a three dimensional projection view format. For three dimensional presentation, a sequence of spatially consecutive and approximately parallel power Doppler image frames are scanned and the received scanlines are stored in the 3D power Doppler memory 502. The frames in the sequence are not scan converted individually and saved, for this would require a considerable storage area for the scan converted images with their interpolated scanlines. Instead, the scanlines of the sequence of frames are scan converted repetitively for each viewing angle of the three dimensional projection image. As each frame is scan converted it is immediately rendered into the three dimensional display. The frames of received scanlines are repetitively scan converted and rendered into three dimensional images of incrementally different viewing angles to present a three dimensional image of a volume of the body which appears to be rotating about one or more of its axes.

Figure 19:
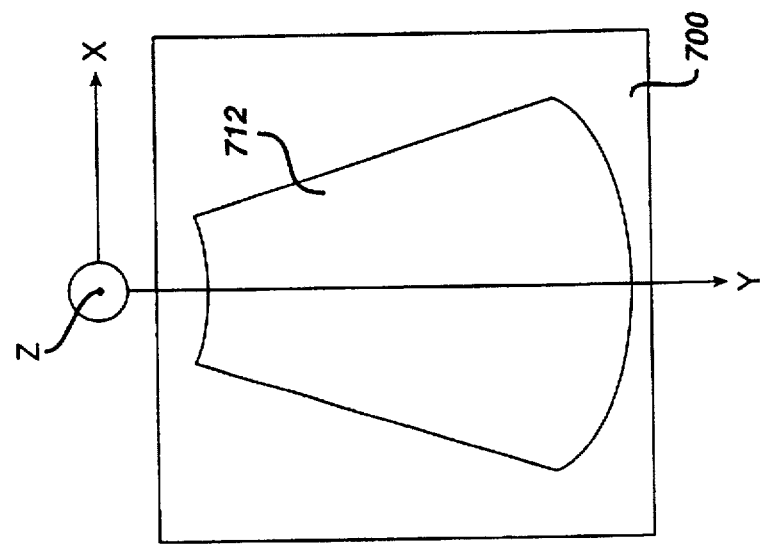

By way of example, suppose that six parallel image frames are acquired at incrementally increasing depths in the z direction. FIG. 19 illustrates these image frames when aligned in parallel with the z dimension extending into the drawing. The image frames therefore are fully aligned so that only the top image frame 700 is visible; the other image frames 702–710 are behind image frame 700. Each image frame includes an image sector 712, one of which is visible on top in FIG. 19.

Figure 20:
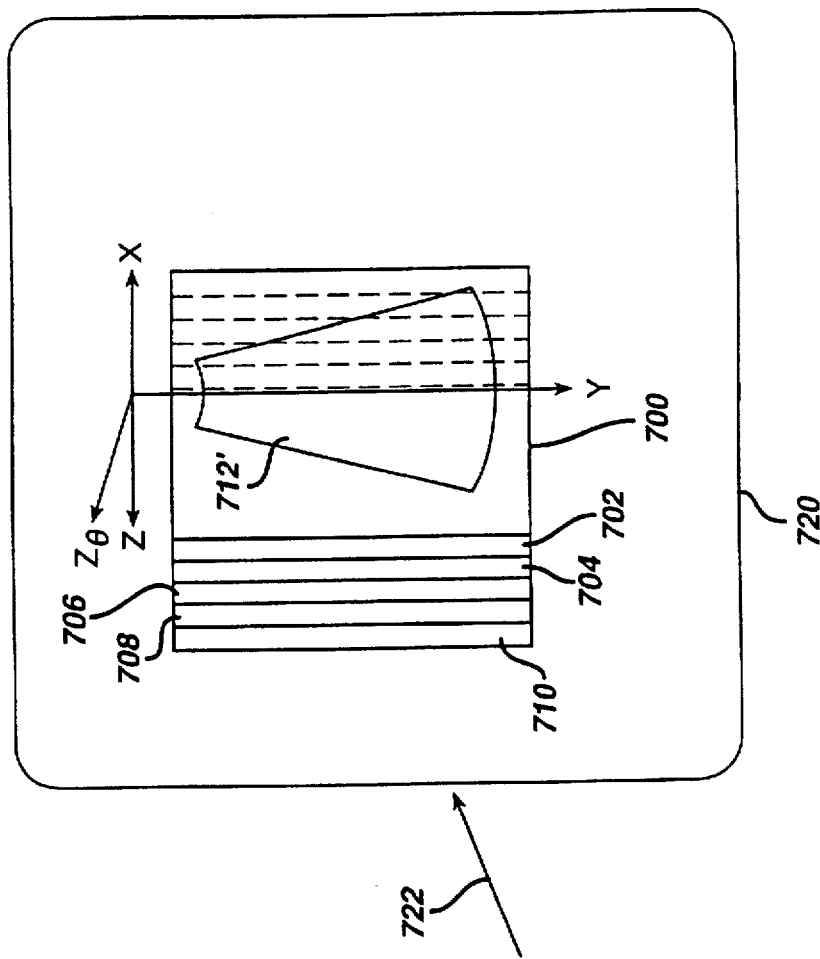
FIGS. 19 and 20 illustrate three dimensional rendering using two dimensional image frames.

Now suppose that the image frames 700–710 of FIG. 19 are rotated about a centroid y axis, as shown in FIG. 20. The edges of the obscured frames 702–710 now become visible by reason of the rotation. The rotation shifts the orientation of the z axis to a rotated direction $z_\theta$. In a handheld ultrasound system of the present invention a three dimensional projection image is formed of this rotated image set, projected as if the viewer is viewing the image planes through a viewing window 720 and at a viewing angle 722. It is seen that the sector 712 has become compressed in its x dimension when rotated, as shown by sector 712 in FIG. 20, which permits the scan conversion techniques of U.S. Pat. No. 5,485,842 to be employed to render a three dimensional presentation. In accordance with the present invention, the three dimensional rendering is done by addressing the planar frame data through efficient accumulation of address constants in accumulators.

For ease of illustration an example of three dimensional processing will be given for rotation about the y axis. This means that a scan converted image will have the same y row coordinates when the image frame set is rotated by an angle θ, or $Y_\theta = y$. The other coordinates are expressed in matrix form as:

$$\begin{bmatrix} z_\theta \\ x_\theta - x_{c\theta} \end{bmatrix} = \begin{bmatrix} \cos\theta & \sin\theta \\ -\sin\theta & \cos\theta \end{bmatrix} \begin{bmatrix} z \\ x - x_{cd} \end{bmatrix} \quad (4)$$

where $z_\theta$ and $x_\theta$ are the x and y coordinates in the θ rotated coordinate system, z is the number of an image frame in the sequence, $x_{c\theta}$ is the centroid of the image frame set in the viewing window 720, and $x_{cd}$ is the center of a particular image frame. Solving for x yields $$x = \frac{x_\theta}{\cos\theta} + x_{cd} - \frac{x_{c\theta}}{\cos\theta} + z\tan\theta \quad (5)$$

of which the latter three terms are constants used to initialize the x address for three dimensional projection.

The received scanlines from a Doppler image frame are scan converted as described previously, and the scan converted and interpolated planar image is projected into a 3D buffer which stores the three dimensional projection image. The pixels in the scan converted image are processed row by row and pixel by pixel to project the Doppler values to their positions in the three dimensional image presentation. Rows of both the planar image and the 3D buffer are sequentially addressed by a y address accumulator that simply accumulates integers to sequentially process image row 1, image row 2, and so forth. The x addresses of the 3D buffer are incremented across each row in integer form by a counter which counts in the sequence 1, 2, 3, and so forth.

The x addresses of the planar image start from an initial value formed by the latter three constant terms of expression (5). Each projection image of the 3D buffer exhibits a different projection angle θ, and thus a constant value of tanθ is calculated and used for processing of a projection image. The center of the 3D image centroid $x_{c\theta}$ is a known constant for a given 3D projection image sequence and the center of each planar image $x_{cd}$ is a known constant for each planar image. Thus, from expression (5), the x address for converting the planar image starts from $$x_{init} = x_{cd} - \frac{x_{c\theta}}{\cos\theta} + z\tan\theta \quad (6)$$

The $x_{init}$ value for a given planar image and given viewing angle θ is calculated and stored, and used to initialize the first x address location in each row y of the planar image. Successive addresses are produced from this initial x address by adding the constant value of 1/cosθ to the previous address, and relocating each addressed value of the planar image to successive x address locations across each row of the three dimensional projection image. As each row is finished, the y row address is incremented by one, the x address of the planar image is reinitialized to $X_{init}$, and the process continues down each row of the planar image until the complete image has been relocated to the projection image.

After one planar image has been relocated to the projection image, the value of ztanθ is incremented to the next z value. Thus, the sequence of ztanθ values will proceed from tanθ to 2tanθ to 3tanθ and so forth through the sequence of planar images. Each new ztanθ value is used in the calculation of a new $x_{init}$ value for the next planar image in the sequence in accordance with expression (6).

There are a number of ways of combining the planar image information in the projection image. One technique is the maximum intensity technique whereby, if a value from a previous planar image has already been stored in the projection image location, the next value to be stored in the same location is compared with the previously stored value. The greater of the two values is then stored. Thus, the projection image will contain the maximum intensity value at each location in the rendered projection image.

A second combining technique which imparts a semi transparent characteristic to the projection image is an averaging technique. Each new value for a given projection image location is averaged with the values previously stored at the location, so that the resultant image reflects not the maximum intensity, but an average through the planar image set. Depending upon whether the planar image processing proceeds from the front or the back image of the set, the projection image will be weighted in favor of the planar images closest to the viewer, or in favor of the planar images most distant from the viewer, or the values can be weighted in accordance with the distance of their z value from the viewing window 720. The technique chosen by the viewer is one of personal preference.

The foregoing three dimensional presentation technique advantageously conserves memory by storing only received scanlines. There is no need to expend storage on a full interpolated image set, as interpolation is performed as each projection image is formed. The inventive technique utilizes efficient addressing by simple incrementing of address accumulators with constant values for each projection image.

Figure 21:
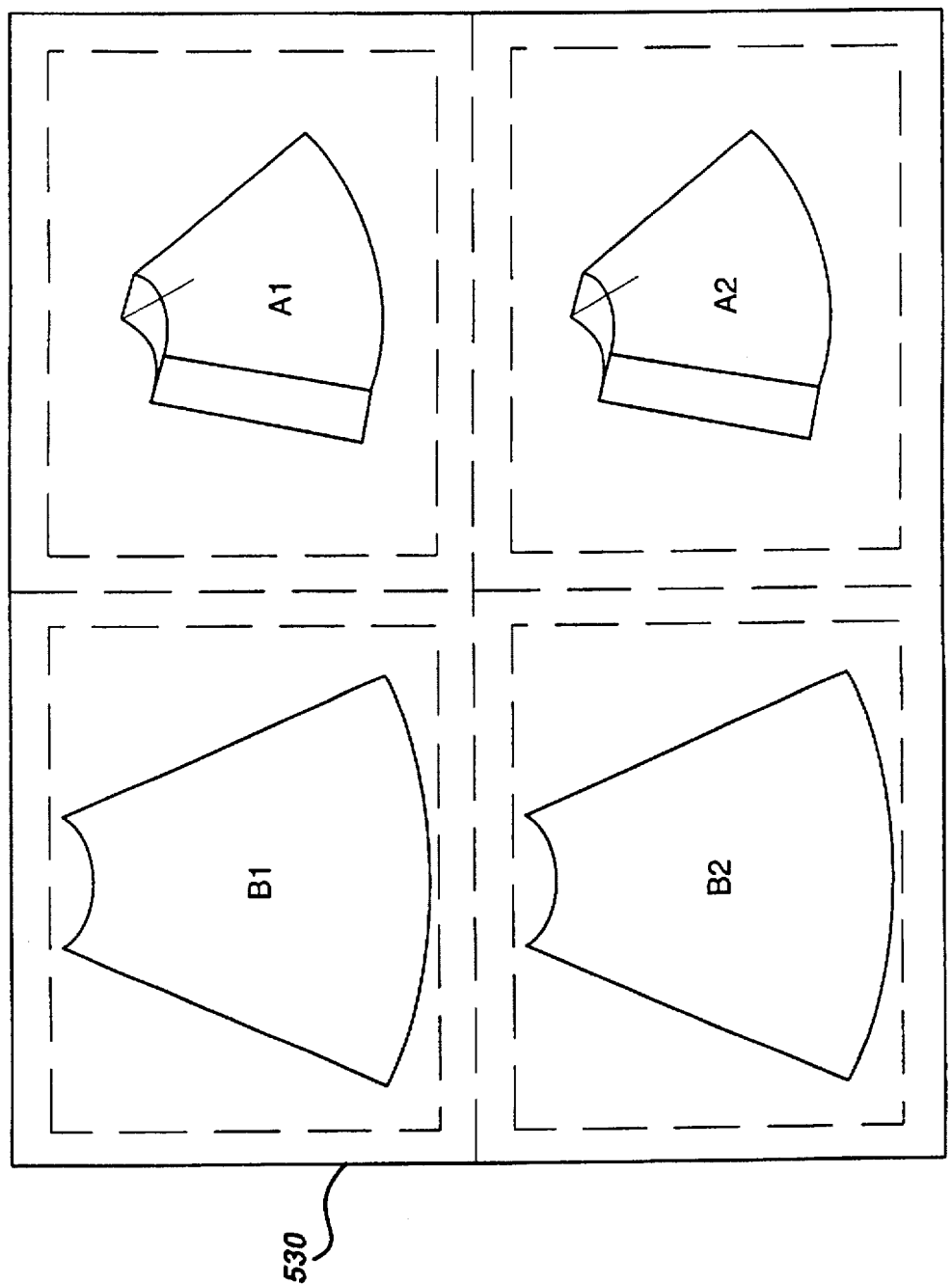
FIG. 21 illustrates the partitioning of the frame buffer memory during three dimensional imaging.

A preferred implementation of three dimensional imaging in accordance with the present invention makes efficient use of the frame buffer memory 530 by partitioning the memory into four quadrants as shown in FIG. 21. For instance a first frame of received scanlines is interpolated and scan converted into the memory area identified as B1. The scan converted first planar image in area B1 is relocated to three dimensional projection coordinates in the memory area identified as A1. While this three dimensional projection of the first planar image is taking place, the second frame of received scanlines is interpolated and scan converted into the memory area B2. Then, while the scan converted second planar image in area B2 is projected to the projection coordinates in area A1, the third frame of received scanlines is scan converted into the B1 memory area. Memory areas B1 and B2 are alternatively used by consecutive image frames until the full projection image has been formed in the A1 area.

The projection image in the A1 area is then read out line by line for video display. As the A1 projection image is read out, memory areas B1 and B2 again scan convert the received frames in alternate fashion and a second projection image at the next viewing angle $\theta$ is assembled in the A2 memory area. After the first projection image has been displayed from the A1 memory area and the second projection image at the next projection angle has been fully assembled in the A2 memory area, the second projection image is read out from area A2 and displayed. The process continues with areas B1 and B2 scan converting the received frames to form a third projection image at a third projection angle in the A1 memory area. Thus, all four quadrants of the buffer memory are interactively used to efficiently produce a three dimensional projection which appears to rotate about the y axis before the viewer.

For rotation about two axes simultaneously, a second projection of the planar images must be performed to rotate the coordinates from an intermediate coordinate system $\theta$ to a final coordinate system $\phi$. For example, after the planar image set has been rotated about the y axis by an angle $\theta$, the image coordinates can be translated a second time by rotation through an angle $\phi$ about the x axis. For the second coordinate transformation $x_{100}$ is set equal to $x_\theta$, the value of z in matrix expression (5) is set to $z_{74}$, and $z_\theta$ on the left side of the matrix is set to $z_\phi$. The matrix expression is solved for y and the second coordinate transformation performed to the twice rotated coordinate values. The second transformation of coordinates required for each planar image for each projection image will increase the time required to produce the three dimensional presentation.

It will be appreciated that there is no need to perform coordinate transformation on pixels outside the area of sector 712 in each planar image. Since the sector area should be identical from one scan converted image to another and occupy known coordinates in each image, it is possible to improve processing speed by only converting and projecting image information within the sector area.

The back end ASIC 50 is the location of the RISC processor 500, which is used to coordinate the timing of all of the operations of the handheld ultrasound system. The RISC processor is connected to all other major functional areas of the ASICS to coordinate processing timing and to load buffers and registers with the data necessary to perform the type of processing and display desired by the user. Program data for operation of the RISC processor is stored in a program memory 52 which is accessed by the RISC processor. Timing for the RISC processor is provided by clock signals from the clock generator on the front end ASIC 30. The RISC processor also communicates through a PCMCIA interface, by which the processor can access additional program data or transmit image information remotely. The PCMCIA interface can connect to a telemetry link or a modem for the transmission of ultrasound images from the handheld unit to a remote location, for instance.

The RISC processor is operated under user control by commands and entries made by the user on the user control 70. A chart showing control functions, the type of controls, and their description is shown in FIG. 22. It will be appreciated that a number of functions, such as patient data entry, Cineloop operation, and 3D review, will operate through menu control to minimize the number of key or button controls on the small handheld unit. To further simplify the unit a number of operating functions are preprogrammed to specific diagnostic applications and will operate automatically when a specific application is selected. Selection of B mode imaging will automatically invoke frequency compounding and depth dependent filtering, for instance, while a four multiplier filter will automatically be set up as a wall filter when Doppler operation is selected. The menu selection of specific clinical applications can automatically invoke specific feature settings such as TGC control characteristics and focal zones, for example.

What is claimed is:
1. A portable ultrasound system comprising:
   an array transducer; and
   a sampled data beamformer for delaying and combining samples of echo signals received by elements of said array transducer,
   wherein said array transducer and said beamformer are located in a common enclosure.
2. The portable ultrasound system of claim 1, wherein said array transducer is a linear array.
3. The portable ultrasound system of claim 1, wherein said array transducer is a curved linear array.
4. The portable ultrasound system of claim 1, further comprising means for sampling echo signals received by said array transducer.
5. The portable ultrasound system of claim 4, wherein said means for sampling echo signals comprises analog to digital converters.
6. The portable ultrasound system of claim 5, wherein said beamformer is a digital beamformer, coupled to receive echo signal samples from said analog to digital converters, which delays and combines digital echo signals.
7. The portable ultrasound system of claim 1, wherein said beamformer is a digital beamformer which delays and combines digital echo signals.
8. The portable ultrasound system of claim 1, wherein said common enclosure is suitable for being held by an operator to ultrasonically scan the body of a patient for reception of echo signals by said array transducer.

9. The portable ultrasound system of claim 1, wherein said sampled data beamformer is fabricated on an integrated circuit chip.

10. The portable ultrasound system of claim 9, wherein said integrated circuit chip is an application specific integrated circuit.

11. A handheld ultrasound system comprising:

an array transducer; and a sampled data beamformer for delaying and combining samples of echo signals received by elements of said array transducer, wherein said array transducer and said beamformer are located in one or more enclosures weighing less than ten pounds (4.5 kilograms).

12. The handheld ultrasound system of claim 11, further comprising a digital filter coupled to the output of said beamformer and located in the same enclosure as said beamformer.

13. The handheld ultrasound system of claim 11, further comprising an image processor coupled to the output of said digital filter and located in the same enclosure as said digital filter.

14. The handheld ultrasound system of claim 13, further comprising an image display coupled to the output of said image processor.

15. The handheld ultrasound system of claim 14, wherein said beamformer, said digital filter, and said image processor are located in a first enclosure, and said image display is located in a second enclosure.

16. The handheld ultrasound system of claim 11, wherein said beamformer is a digital beamformer which delays and combines digital echo signals.

17. The handheld ultrasound system of claim 16, further comprising a digital filter and an image processor located in a common enclosure with said digital beamformer.

18. The handheld ultrasound system of claim 17, wherein said image processor includes a digital scan converter.

19. A handheld ultrasound system comprising:

a transducer;

a B mode signal processor; and a Doppler signal processor, wherein said transducer, said B mode signal processor and said Doppler signal processor are located in a common handheld enclosure.

20. The handheld ultrasound system of claim 19, wherein said common handheld enclosure weighs less than ten pounds (4.5 kilograms).

21. The handheld ultrasound system of claim 20, further comprising a digital beamformer located in said common handheld enclosure.

22. A handheld ultrasound system comprising:

an array transducer; and a beamformer integrated circuit for delaying and combining echo signals received by elements of said array transducer, wherein said array transducer and said beamformer integrated circuit are located in a handheld enclosure, wherein said beamformer integrated circuit comprises a sampled data beamformer.

23. The handheld ultrasound system of claim 22, wherein said sampled data beamformer comprises a digital beamformer.

24. A handheld ultrasound system comprising:

an array transducer; and a beamformer integrated circuit for delaying and combining echo signals received by elements of said array transducer, wherein said array transducer and said beamformer integrated circuit are located in a handheld enclosure;

further comprising an image processing integrated circuit for producing image signals in response to echo signals produced by said beamformer integrated circuit, wherein said image processing integrated circuit comprises a digital scan converter.

* * * * *